United States Patent [19]

Chatterjee

[11] Patent Number: 5,270,179
[45] Date of Patent: Dec. 14, 1993

[54] CLONING AND EXPRESSION OF T5 DNA POLYMERASE REDUCED IN 3'- TO-5' EXONUCLEASE ACTIVITY

[75] Inventor: Deb K. Chatterjee, N. Potomac, Md.

[73] Assignee: Life Technologies, Inc., Gaithersburg, Md.

[21] Appl. No.: 826,945

[22] Filed: Jan. 28, 1992

Related U.S. Application Data

[63] Continuation-in-part of Ser. No. 698,786, May 13, 1991, abandoned, and a continuation-in-part of Ser. No. 494,531, Mar. 16, 1990, which is a continuation of Ser. No. 391,930, Aug. 10, 1989, Pat. No. 5,047,342.

[51] Int. Cl.$^5$ .................... C12P 21/02; C12N 9/12
[52] U.S. Cl. .................... 435/69.1; 435/69.8; 435/69.7; 435/193; 435/191; 435/172.3; 435/320.1; 435/252.3; 435/252.33; 435/194; 536/23.1; 536/23.2; 536/23.72; 536/24.1; 536/24.2; 536/23.4; 935/6; 935/14; 935/38; 935/72
[58] Field of Search ........... 435/69.1, 191, 193, 435/194, 172.3, 320.1, 252.3, 252.33, 69.7, 69.8; 536/27, 23.1, 23.2, 23.72, 24.1, 24.2, 23.4; 935/6, 14, 38, 72, 73

[56] References Cited

U.S. PATENT DOCUMENTS

| | | | |
|---|---|---|---|
| 4,394,443 | 7/1983 | Weissman et al. | 435/6 |
| 4,689,406 | 8/1987 | Banks et al. | 435/172.3 |
| 4,766,066 | 8/1988 | Kuhstoss et al. | 435/91 |
| 4,795,699 | 1/1989 | Tabor et al. | 435/5 |
| 4,889,818 | 12/1989 | Gelfand et al. | 435/194 |
| 5,047,342 | 9/1991 | Chatterjee | 435/194 |
| 5,102,802 | 4/1992 | McAllister | 435/252.33 |

FOREIGN PATENT DOCUMENTS

| | | |
|---|---|---|
| 0265293 | 4/1988 | European Pat. Off. |
| WO89/06691 | 7/1989 | PCT Int'l Appl. |

OTHER PUBLICATIONS

Bernad et al., "A Conserved 3'-5'Exonuclease Active Site in Prokariotic and Eukariotic DNA Polymerases", Cell 59:219-228 (1989).

Boehringer Mannheim catalog, p. 317.

Das et al., "Effect of Magnesium CTP(2-) and Magnesium GTP(2-) on the 3'-5' Exonuclease Activity of T5-Induced DNA Polymerase", Chem. Abstracts 91(1):194 ref No. 1841R (1979).

Das et al., "Mechanism of T-5-Induced DNA Polymerase", J. of Biological Chem. 252(10):8700-8707 (1977).

Das et al., "Processiveness of DNA Polymerases", J. of Biological Chem. 254(4):1227-1232 (1979).

Das et al., "Mechanism of Primer-Template-Dependent Conversion of dNTP→dNMP by T5 DNA Polymerase", J. of Biological Chem. 255(15):7149-7154 (1980).

Das et al., "Effect of Mg·CTP$^{2-}$ and Mg·GTP$^{2-}$ on the 3'→5' Exonuclease Activity of T5-Induced DNA Polymerase", J. Carbohydr., Nucleosides, Nucleotides 5(5):457-467 (1978).

Fujimura et al., "Characterization of DNA Polymerase Induced by Bacteriophage T5 with DNA Containing Single Strand Breaks", J. of Biological Chem. 251:2168-2175 (1976).

Johnson et al., "Elementary Steps of DNA Polymerization", DNA Protein Interaction—8th Summer Sympo-
(List continued on next page.)

Primary Examiner—Christopher S. F. Low
Attorney, Agent, or Firm—Sterne, Kessler, Goldstein & Fox

[57] ABSTRACT

The present invention discloses a recombinant DNA molecule having a full length or a truncated T5 DNA polymerase structural gene, each encoding a processive, thioredoxin-independent DNA polymerase. The DNA polymerase of the invention may have 3'-to-5'exonuclease activity or may be substantially reduced in processive 3'-to-5'DNA exonuclease activity. A method for producing these enzymes is also disclosed, as is the proteins produced by this process. The present invention is also directed to a leader sequence important for expression of soluble T5 DNA polymerase protein.

29 Claims, 11 Drawing Sheets

OTHER PUBLICATIONS

*sium in Molecular Biology*, Penn. St. Univ., Jul. 26–28, 1989 (Abstracts) pp. 44, 60–62.

Joyce et al., "DNA Polymerase I: from Crystal Structure to Function Via Genetics", *Trends Biochem. Sci.* 12:288–292 (1987).

Kozak, "Comparison of Initiation of Protein Synthesis in Procaryotes, Eucaryotes, and Organelles", *Microbiological Reviews* 47(1):1–45 (1983).

Leavitt et al., "T5 DNA Polymerase: Structural-Functional Relationships to Other DNA Polymerases", *Proc. Natl. Acad. Sci. USA* 86:4465–4469 (1989).

Lin et al., "Cloning and Expression of T4 DNA Polymerase", *Proc. Natl. Acad. Sci. USA* 84:7000–7004 (1987).

Minkley et al., "*Escherichia coli* DNA Polymerase I", *J. of Biological Chem.* 259(16):10386–10392 (1984).

Reha-Krantz et al., "DNA Polymerization in the Absence of Exonucleolytic Proofreading: In Vivo and In Vitro Studies", *Proc. Natl. Acad. Sci. USA* 88:2417–2421 (1991).

Rhoades, "New Physical Map of Bacteriophage T5 DNA", *J. Virol.* 43(2):566–573 (1982).

Spicer et al., "Primary Structure of T4 DNA Polymerase", *J. of Biological Chem.* 263(16):7478–7486 (1988).

Stueber et al., "A Novel In Vitro Transcription-Translation System: Accurate and Efficient Synthesis of Single Proteins from Cloned DNA Sequences", *EMBO J.* 3(13):3143–3148 (1984).

Tabor et al., "Selective Inactivation of the Exonuclease Activity of Bacteriophage T7 DNA Polymerase by in Vitro Mutagenesis", *J. of Biological Chem.* 264(11):6447–6458 (1989).

Boswell et al., "Sequence Comparison and Alignment: the Measurement and Interpretation of Sequence Similarity", *Computational Molecular Biology*, pp. 161–163 (1988) Ed. Arthur Lesk, Oxform Univ. Press, New York.

Lewin, R., "When Does Homology Mean Something Else?", *Science* 237:1570 (1987).

Fujimura et al., "Physical Locus of the DNA Polymerase Gene and Genetic Maps of Bacteriophage T5 Mutants", *J. of Virology* 53(2):495–500 (1985).

Reeck et al., "'Homology' in Proteins and Nucleic Acids: A Terminology Muddle and a Way Out of IT", *Cell* 50:667 (1987).

Remaut et al., "Plasmid Vectors for High-Efficiency Expression Controlled by the $p_L$ Promoter of Coliphage λ", *Gene* 15:81–93 (1981).

Shibui et al., "A New Hybrid Promoter and Its Expression Vector in *Escherichia coli*", *Agric. Biol. Chem.* 52(4):983–988 (1988).

Stark, M., "Multicopy Expression Vectors Carrying the lac Repressor Gene for Regulated High-Level Expression of Genes in *Escherichia coli*", *Gene* 51:255–267 (1987).

Donlin et al., "Kinetic Partitioning Between the Exonuclease and Polymerase Sites in DNA Error Correction", *Biochemistry* 30:538–546 (1991).

Patel et al., "Pre-Steady-State Kinetic Analysis of Processive DNA Replication Including Complete Characterization of an Exonuclease-Deficient Mutant", *Biochemistry* 30:511–525 (1991).

Wong et al., "An Induced-Fit Kinetic Mechanism for DNA Replication Fidelity: Direct Measurement by Singe-Turnover Kinetics", *Biochemistry* 30: 526–537 (1991).

Creighton, T. E., 1983. in: *Proteins: Structure and Molecular Principles*. W. H. Freeman and Co. New York. pp. 93–95.

Watson, J. D., 1987. in *Molecular Biology of the Gene*. Benjamin/Cummings Publishing Co., Calif. p. 313.

Chatterjee et al., Cloning and overexpression of the gene encoding bacteriophage T5 DNA polymerase, *Gene* 97:13–19 (1991).

LEAVITT & ITO

METTyrSerIleCysValThrArgSerCysProValValCysSerLysLysHisIleThr...
...ATGTATTCCATATGTGTAACGAGAAGTTGTCCGGTCGTTGCTCAAAAAGCATATTACT...
(5')  +1----+----+----+----+----+----+ 60  (3')
...ATGTATTCCATATGTAACGAGAAGTGTCCGGTCGTTGCTC-AAAAAGCATATTACT...
METCysAsnGluLysLeuSerGlyArgLeuLeu-LysLysHisIleThr...
CORRECTED SEQUENCE

FIG.1

NH$_2$-Met-Lys-Ile-Ala-Val-Val-Asp-Lys-Ala-Leu-Asn-Asn-Thr-Arg-Tyr-Asp-Lys-His-Phe-Gln-Leu-Tyr-Gly-Glu-Val-Asp-Val-Phe-His-Met-Cys-Asn-Glu-Lys-Leu-Ser-Gly-Arg-Leu-Leu-Lys-Lys-His-Ile-Thr---- [FULL LENGTH T5 DNA POLYMERASE]

NH$_2$-Met-Cys-Asn-Glu-Lys-Leu-Ser-Gly-Arg-Leu-Leu-Lys-Lys-His-Ile-Thr---- [TRUNCATED T5 DNA POLYMERASE]

FIG.7

```
CCCGGGGTGA CTTAAATAAA GAAGAGATTG ATACGTTAGC AAAACGTATT GAAATTTTAG    60
       -35                                -10
TTGCT GAATC GCTTAAAGAT TTGG TATAAT ATATTGGTAA GTTAGAGAAG AAACACTGAA   120
            RBS
         3→                         7→
GTTATACTTA CTTACCAAGA GGAGATTAAA TTTG AAAATC GCTATACGGC GCAGTAGTTG ATAAAGTCT   180
                                                                  RBS
AAACAACACT CGT TATGAT A AACATTTCCA GCTATACGGC GCTCAAAAAG CATATTACTA TCGGAACTCC   240
                                                          4→2→
                                                         ATG TATTCCA
TAT GTAAC GAGAAGTTGT CCGGTCGTTT GCTCAAAAAG CATATTACTA TCGGAACTCC   300
GGAAAACCCA TTTGACCCGA ATGATTATGA AAGGTATTGG TGATTATACC GGTAAAGTGT TAGAGTATAA   360
CCTGTACTTT GCAGGTAAGA AGGTATTGG CCCAGCCCAG TATCCACGAT ATTATCAATG GTCGTGAGAA   420
TGGATATGCT AACTGGATTG CGAGTATCAG CAGTAGAGAA TATCCACGAT ATTATCAATG GTCGTGAGAA   480
GAAACCAGTT TTTGATGCAA CAGTAGAGAA TATCCACGAT ATTATCAATG GTCGTGAGAA   540
GATTGCAAAA GCTGGTGATT ACCGTCCTAT TACTGACCCT GATGAGGCTG AAGAATATAT   600
CAAGATGGTG TATAATATGG TTATCGGACC CGTCGGATTC GACTCCGAAA CCTCAGCACT   660
ATACTGTCGA GATGGTTATC TGCTTGGTGT TTCTATTCT CACCAAGAGT ATCAGGGTGT   720
ATATATCGAT
```

FIG. 8

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 41 base pairs
( B ) TYPE: nucleic acid
( C ) STRANDEDNESS: both
( D ) TOPOLOGY: both ( x i ) SEQUENCE DESCRIPTION: SEQ ID NO:1:

GGTTATCGGG CCCGTCGCAT TCGCCTCCGC AACCTCAGCA C    41

( 2 ) INFORMATION FOR SEQ ID NO:2:

( i ) SEQUENCE CHARACTERISTICS:
( A ) LENGTH: 10 amino acids
( B ) TYPE: amino acid (C) STRANDEDNESS: double
(D) TOPOLOGY: both (xi) SEQUENCE DESCRIPTION: SEQ ID NO:2:

```
Met Lys Ile Ala Val Val Asp Lys Ala Leu
 1           5                       10
```

(2) INFORMATION FOR SEQ ID NO:3:

(i) SEQUENCE CHARACTERISTICS:
        (A) LENGTH: 30 amino acids
        (B) TYPE: amino acid
        (C) STRANDEDNESS: both
        (D) TOPOLOGY: both (xi) SEQUENCE DESCRIPTION: SEQ ID NO:3:

```
Met Lys Ile Ala Val Val Asp Lys Ala Leu Asn Asn Thr Arg Tyr Asp
 1           5                       10                      15

Lys His Phe Gln Leu Tyr Gly Glu Glu Val Asp Val Phe His
            20                  25                  30
```

(2) INFORMATION FOR SEQ ID NO:4:

(i) SEQUENCE CHARACTERISTICS:
        (A) LENGTH: 60 base pairs
        (B) TYPE: nucleic acid
        (C) STRANDEDNESS: both
        (D) TOPOLOGY: both (ix) FEATURE:
        (A) NAME/KEY: CDS
        (B) LOCATION: 1..60

(xi) SEQUENCE DESCRIPTION: SEQ ID NO:4:

```
ATG TAT TCC ATA TGT GTA ACG AGA AGT TGT CCG GTC GTT TGC TCA AAA      48
Met Tyr Ser Ile Cys Val Thr Arg Ser Cys Pro Val Val Cys Ser Lys
 1               5                      10                  15

AAG CAT ATT ACT                                                      60
Lys His Ile Thr
             20
```

(2) INFORMATION FOR SEQ ID NO:5:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:5:

```
Met Tyr Ser Ile Cys Val Thr Arg Ser Cys Pro Val Val Cys Ser Lys
 1               5                      10                  15

Lys His Ile Thr
             20
```

(2) INFORMATION FOR SEQ ID NO:6:

(i) SEQUENCE CHARACTERISTICS:
        (A) LENGTH: 59 base pairs
        (B) TYPE: nucleic acid
        (C) STRANDEDNESS: both
        (D) TOPOLOGY: both (ix) FEATURE:
        (A) NAME/KEY: CDS
        (B) LOCATION: 12..59

(xi) SEQUENCE DESCRIPTION: SEQ ID NO:6:

```
ATGTATTCCA T ATG TGT AAC GAG AAG TTG TCC GGT CGT TTG CTC AAA AAG    50
```

```
            Met Cys Asn Glu Lys Leu Ser Gly Arg Leu Leu Lys Lys
             1           5                   10
CAT ATT ACT                                                                              59
His Ile Thr
     15
```

( 2 ) INFORMATION FOR SEQ ID NO:7:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met Cys Asn Glu Lys Leu Ser Gly Arg Leu Leu Lys Lys His Ile Thr
 1           5                   10                  15
```

( 2 ) INFORMATION FOR SEQ ID NO:8:

( i ) SEQUENCE CHARACTERISTICS:
        ( A ) LENGTH: 46 amino acids
        ( B ) TYPE: amino acid
        ( C ) STRANDEDNESS: both
        ( D ) TOPOLOGY: both ( x i ) SEQUENCE DESCRIPTION: SEQ ID NO:8:

```
    Met Lys Ile Ala Val Val Asp Lys Ala Leu Asn Asn Thr Arg Tyr Asp
     1           5                   10                  15

Lys His Phe Gln Leu Tyr Gly Glu Glu Val Asp Val Phe His Met Cys
                 20                  25                  30

Asn Glu Lys Leu Ser Gly Arg Leu Leu Lys Lys His Ile Thr
                 35                  40                  45
```

( 2 ) INFORMATION FOR SEQ ID NO:9:

( i ) SEQUENCE CHARACTERISTICS:
        ( A ) LENGTH: 16 amino acids
        ( B ) TYPE: amino acid
        ( C ) STRANDEDNESS: both
        ( D ) TOPOLOGY: both ( x i ) SEQUENCE DESCRIPTION: SEQ ID NO:9:

```
    Met Cys Asn Glu Lys Leu Ser Gly Arg Leu Leu Lys Lys His Ile Thr
     1           5                   10                  15
```

( 2 ) INFORMATION FOR SEQ ID NO:10:

( i ) SEQUENCE CHARACTERISTICS:
        ( A ) LENGTH: 730 base pairs
        ( B ) TYPE: nucleic acid
        ( C ) STRANDEDNESS: both
        ( D ) TOPOLOGY: both ( x i ) SEQUENCE DESCRIPTION: SEQ ID NO:10:

```
CCCGGGGTGA CTTAAATAAA GAAGAGATTG ATACGTTAGC AAAACGTATT GAAATTTTAG      60

TTGCTGAATC GCTTAAAGAT TTGGTATAAT ATATTGGTAA GTTAGAGAAG AAACACTGAA     120

GTTATACTTA CTTACCAAGA GGAGATTAAA TTTGAAAATC GCAGTAGTTG ATAAAGCTCT     180

AAACAACACT CGTTATGATA AACATTTCCA GCTATACGGC GAGGAAGTTG ATGTATTCCA     240

TATGTGTAAC GAGAAGTTGT CCGGTCGTTT GCTCAAAAAG CATATTACTA TCGGAACTCC     300

GGAAAACCCA TTTGACCCGA ATGATTATGA TTTTGTTATA CTGGTAGGTG CCGAACCTTT     360

CCTGTACTTT GCAGGTAAGA AAGGTATTGG TGATTATACC GGTAACGTG TAGAGTATAA      420
```

| | | | | | |
|---|---|---|---|---|---|
| TGGATATGCT | AACTGGATTG | CGAGTATCAG | CCCAGCCCAG | TTACACTTTA | AACCTGAAAT | 480
| GAAACCAGTT | TTTGATGCAA | CAGTAGAGAA | TATCCACGAT | ATTATCAATG | GTCGTGAGAA | 540
| GATTGCAAAA | GCTGGTGATT | ACCGTCCTAT | TACTGACCCT | GATGAGGCTG | AAGAATATAT | 600
| CAAGATGGTG | TATAATATGG | TTATCGGACC | CGTCGCATTC | GACTCCGAAA | CCTCAGCACT | 660
| ATACTGTCGA | GATGGTTATC | TGCTTGGTGT | TTCTATTTCT | CACCAAGAGT | ATCAGGGTGT | 720
| ATATATCGAT | | | | | | 730

CLONING AND EXPRESSION OF T5 DNA POLYMERASE REDUCED IN 3'- TO-5' EXONUCLEASE ACTIVITY

RELATED APPLICATIONS

This application is a continuation-in-part of application Ser. No. 07/698,786, filed May 13, 1991 now abandoned, which is a continuation of application Ser. No. 07/391,930, filed Aug. 10, 1989 (now U.S. Pat. No. 5,047,342), and a continuation-in-part of application Ser. No. 07/494,531, filed Mar. 16, 1990. Each of these applications and/or patents are herein incorporated by reference in their entirety.

FIELD OF THE INVENTION

This invention relates to molecular cloning and expression of the DNA polymerase of the *E. coli* bacteriophage T5 and to production of mutants of T5 DNA polymerase substantially reduced in 3'-to-5' exonuclease activity.

BACKGROUND OF THE INVENTION

DNA polymerases synthesize the formation of DNA molecules from deoxynucleoside triphosphates using a complementary template DNA strand and a primer. DNA polymerases synthesize DNA in the 5'-to-3' direction by successively adding nucleotides to the free 3'-hydroxyl group of the growing strand. The template strand determines the order of addition of nucleotides via Watson-Crick base pairing. In cells, DNA polymerases are involved in repair synthesis and DNA replication.

Bacteriophage T5 induces the synthesis of its own DNA polymerase upon infection of its host, *Escherichia coli*. The T5 DNA polymerase (T5-DNAP) was purified to homogeneity by Fujimura RK & Roop BC, J. Biol. Chem. 25:2168–2175 (1976). T5-DNAP is a single polypeptide of molecular weight of about 96 kilodaltons. This polymerase is highly processive and, unlike T7 DNA polymerase, does not require thioredoxin for its processivity (Das SK & Fujimura RK, J. Biol. Chem. 252:8700–8707 (1977); Das SK & Fujimura RK, J. Biol. Chem. 254:1227–1237 (1979)).

Fujimura RK et al., J. Virol. 53:495–500 (1985) disclosed the approximate location of the T5-DNAP gene on the physical restriction enzyme map generated by Rhoades (J. Virol. 43:566–573 (1982)). DNA sequencing of the fragments of this corresponding region was disclosed by Leavitt MC & Ito J, Proc. Natl. Acad. Sci. USA 86:4465–4469 (1989). However, the authors did not reassemble the sequenced fragments to obtain expression of the polymerase.

Oligonucleotide-directed, site-specific mutation of a T7 DNA polymerase gene was disclosed by Tabor S & Richardson CC, J. Biol. Chem. 264:6447–6458 (1989).

The existence of a conserved 3'-to-5' exonuclease active site present in a number of DNA polymerases was predicted by Bernad A et al., Cell 59:219–228 (1989).

In molecular biology, DNA polymerases have several uses. In cloning and gene expression experiments, DNA polymerases are used to synthesize the second strand of a single-stranded circular DNA annealed to an oligonucleotide primer containing a mutated nucleotide sequence. DNA polymerases have also been used for DNA sequencing. Tabor & Richardson, U.S. Pat. No. 4,795,699, disclose that processive, host thioredoxin-requiring, T7-type DNA polymerases, especially those lacking substantial exonuclease activity, are very useful for DNA sequencing.

SUMMARY OF THE INVENTION

The DNA polymerase of *E. coli* bacteriophage T5 is distinguished from other DNA polymerases by its high degree of processivity. In other words, a particular T5-DNAP molecule will replicate a single template DNA molecule without dissociation. Das & Fujimura (1977) and (1979), supra, report that T5-DNAP processively synthesizes about 140 to about 200 nucleotides before dissociation. In contrast, other DNA polymerases, such as T4 DNA polymerase, Klenow, and reverse transcriptase, tend to dissociate from the template/newly synthesized strand duplex after only a few bases: a newly synthesized strand will usually have been synthesized by several different enzyme molecules. Similarly, the 3'-to-5' exonuclease activity of T5-DNAP is highly processive; a particular DNA strand will usually be hydrolysed by only one exonuclease molecule. T5-DNAP is also exceptionally good at displacing nicked duplex DNA strands while synthesizing a new strand. Most DNA polymerases need other protein factors or enzymatic activities to accomplish the same result.

These strand displacement and processivity qualities make T5-DNAP a good polymerase to use for DNA sequencing, in a DNA amplification or DNA labeling. T5-DNAP does not need a protein cofactor to be active or processive, in contrast to other polymerases useful for the same biochemical tasks. For example, T7 DNA polymerase, which is also processive and often used for DNA sequencing, needs *E. coli* thioredoxin as a cofactor. Lastly, in infections of *E. coli* by T5 phage, T5-DNAP is present at very low levels, which increases production costs in using the T5-DNAP. To date, this has made commercial production impractical because acceptable alternatives are not available. Therefore, it is an object of the present invention to provide improved means for producing T5 DNA polymerase.

The 3'-to-5' exonuclease activity is undesirable for a DNA sequencing enzyme. Therefore, it is an object of the present invention to obtain T5-DNAP lacking 3'-to-5' exonuclease activity. Mutant T5-DNAP lacking 3'-to-5' exonuclease activity is useful to synthesize DNA, and therefore to sequence DNA, using nucleotide analogs which otherwise would not be incorporated because of 3'-to-5' editing/exonuclease activity.

The present invention is predicated on several discoveries. Fujimura et al. showed that the gene for T5-DNAP is on the SmaI fragment D. Using this information, it should have been possible to clone the gene using a simple, straight-forward cloning strategy. However, Applicant surprisingly discovered that the presence of sequences near the T5-DNAP gene were deleterious to the host cell and thus the gene could not be directly cloned. In order to clone the T5-DNAP gene, the deleterious T5 sequences flanking the T5-DNAP gene, particularly the sequences 5'-to the structural gene, must be removed before it can be cloned in an *E. coli* host cell.

Leavitt & Ito, Proc. Natl. Acad. Sci. USA 86:4465–4469 (1989) disclosed the cloning of fragments of the T5-DNAP gene and the sequencing thereof. These fragments were not reassembled, nor was expression of the gene obtained. Further, the published sequence of Leavitt & Ito is incorrect at its 5'-end (see FIG. 1). Specifically, an extra "A" residue is reported in the region of nucleotides +45 to +50. This mistake corrupts the open reading frame analysis, leading to an improperly derived sequence for the amino-terminus of the protein, substituting an improper polypeptide of 15 amino acid residues for the 11 residue sequence (FIG. 1). Use of this sequence to engineer the T5-DNAP gene would leave excess flanking sequences at the 5'-end, which can lower expression levels. Specifically, it has been discovered that with a construction that places a heterologous ribosome binding site immediately next to a translational initiation codon (at position +12 of the sequence of Leavitt & Ito, supra,, higher levels of enzyme will be produced than with constructions that are identical except for the retention of small amounts of 5'-flanking sequences. Furthermore, use of the published sequence from Leavitt & Ito, in some types of constructions, can lead to translational initiation out of the correct reading frame. For example, a fusion protein initiating 5'-to the sequencing error disclosed in FIG. 1 could be unexpectedly inoperative. Given the herein disclosed teachings, detailed in the Examples, one of ordinary skill in the art can use standard recombinant DNA techniques to practice the preferred embodiments, namely expression of a T5 DNA polymerase in E. coli.

Applicant has recently discovered that the ATG translational initiation codon located at +12 of Leavitt & Ito, supra) generates a truncated form of T5 DNA polymerase, although this truncated protein is active. That is, the truncated T5 DNA polymerase protein has T5 polymerase activity. Applicant has unexpectedly discovered that the full length T5 polymerase structural gene has a TTG initiation codon at −78 of the Leavitt & Ito sequence, supra. The amino acid terminal sequence (N-terminal sequence) of the full length clone (pTTQ19-T5-3 and pSportT5) agree with the N-terminal amino acid sequence of native (wild type) T5 DNA polymerase.

Applicant has also discovered that clones, which used the ATG initiation codon at position +12 of Leavitt & Ito, supra (pUCP$_L$-T5 and pTTQ-T5-2), produced high levels of total cellular protein (approximately 40%). However, the majority of the polymerase protein produced by these clones was insoluble and formed inclusion bodies in the host cell. On the other hand, full length T5 DNA polymerase expressed by clones having the TTG initiation codon at position −78 was completely soluble (no inclusion bodies were detected). Although clones expressing the full length protein (pTTQ19-T5-3 and pSportT5) produced T5 DNA polymerase at levels of about 2-5% of the total cellular protein, higher yields of polymerase protein could be recovered from cells expressing the full length protein compared to cells which produced the truncated form. Thus, although clones expressing the truncated T5 DNA polymerase protein produced higher levels of protein, higher recoveries could be obtained from the clones producing the full length T5 DNA polymerase.

BRIEF DESCRIPTION OF THE DRAWINGS

FIG. 1 is a comparison of the sequences disclosed herein with those published by Leavitt & Ito, Proc. Natl. Acad. Sci. USA 86:4465-4469 (1989). The upper half of the Figure gives Leavitt & Ito's DNA sequence and the protein sequence derived therefrom. The lower half of the Figure gives a DNA sequence and a protein sequence derived therefrom when the ATG at position +12 is used as the initiation codon. The numbering convention is as in Leavitt & Ito unless otherwise noted. The "ATG" translational start codons are in bold letters, as is the location of the extra "A" introduced into the sequence. Note that the exact location of the mistake could be anywhere in the string of "A"s. As noted, the ATG start codon (position +12) is not the native initiation codon of T5 DNA polymerase. However, an active truncated polymerase protein is expressed using this ATG start codon.

FIG. 7 compares the amino acid sequences of the full length and truncated T5 DNA polymerase proteins. These proteins only differ in their N-terminal sequence.

FIG. 8 shows a partial DNA sequence of T5 DNA polymerase showing the native promoter sequence (position 52 to 90), the native ribosomal binding site (position 140), and the TTG initiation codon (position 152). Also shown are the ribosomal binding site and ATG start codon proposed by Leavitt & Ito (supra), at positions 221 and 231, respectively. The ATG initiation codon used for expressing truncated T5 DNA polymerase is shown at position 242.

Exonuclease III was used to remove deleterious 5' sequences of T5 DNA polymerase as described in Example 3. DNA sequences of four clones (clone 2, 3, 4 and 7) are shown in FIG. 8 with their start position indicated by 2→, 3→, 4→ and 7→, respectively. DNA sequence 5' of the indicated start position was removed by exonuclease III for each clone.

Figure 9:
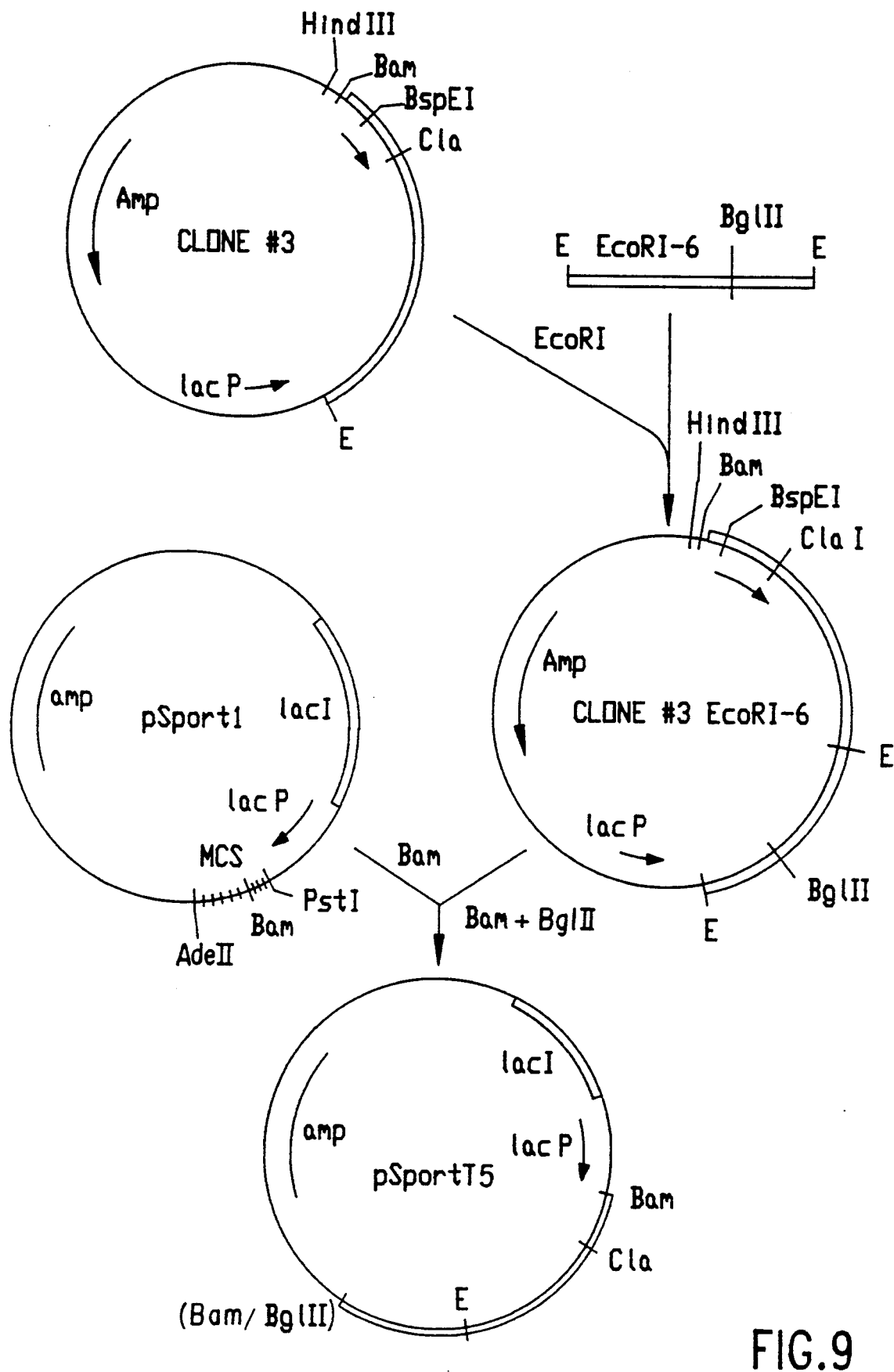

FIG. 9 shows a schematic drawing, not necessarily to scale, of the cloning scheme described in Example 12 to construct pSportT5. Plasmid pSportT5, when carried by a host cell, is capable of expressing full length T5 DNA polymerase protein.

DETAILED DESCRIPTION OF THE INVENTION

The following terms are defined in order to provide a clear and consistent understanding of their use in the specification and the claims. Other terms are well known to the art so that they need not be defined herein.

Amino acid residues are numbered herein as numbered by Leavitt & Ito, supra, unless noted otherwise. Note that the first 15 amino acids disclosed by Leavitt & Ito are incorrect. The N-terminal 11 amino acid residues of the truncated protein of active T5 DNA polymerase protein is compared to the N-terminal sequence of Leavitt & Ito (FIG. 1). Both sequences are correct starting with the Lys[16] residue. The correct (native) N-terminal amino acid sequence is shown in FIG. 7. The full length protein has an additional 30 amino acids at its N-terminal region compared to the truncated protein. This 30 amino acid N-terminal sequence is referred to herein as a "leader sequence." The 30 amino acid "leader sequence" shown in FIG. 7 is important for producing soluble T5 DNA polymerase protein upon expression in a host cell. The "leader sequence" of the invention may also be used at the N-terminal region of proteins other than T5 DNA polymerase to increase the solubility of such proteins. Thus, by using standard recombinant DNA techniques, it is possible to fuse the leader sequence of the invention to the N-terminal region of other heterologous proteins which tend to be insoluble upon expression. It is also possible to replace part of the N-terminal amino acid sequence of the expressed protein with the leader sequence of the invention.

"Structural gene" is a DNA sequence that is transcribed into messenger RNA that is then translated into a sequence of amino acid residues characteristic of a specific polypeptide. As used herein, a structural gene may contain a heterologous ribosome binding site, replacing its natural (homologous) ribosome binding site.

"Soluble" refers to the physical state of a protein upon expression in a host cell, i.e., the protein has the ability to form a solution in vivo. As used herein, a protein is "soluble" if the majority (greater than 50%) of the protein produced in the cell is in solution and is not in the form of insoluble inclusion bodies.

"Nucleotide" is a monomeric unit of DNA or RNA consisting of a sugar moiety, a phosphate, and a nitrogenous heterocyclic base. The base is linked to the sugar moiety via the glycosidic carbon (1' carbon of the pentose). The combination of a base and a sugar is called a nucleoside. Each nucleotide is characterized by its base. The four DNA bases are adenine (A), guanine (G), cytosine (C), and thymine (T). The four RNA bases are A, G, C and uracil (U).

"Processive" is a term of art referring to an enzyme's property of acting to synthesize or hydrolyse a polymer without dissociating from the particular polymer molecule. A processive DNA polymerase molecule can add hundreds of nucleotides to a specific nucleic acid molecule before it may dissociate and start to extend another DNA molecule. Conversely, a non-processive polymerase will add as little as a single nucleotide to a primer before dissociating from it and binding to another molecule to be extended. For the purposes of the present invention, processive refers to enzymes that add, on the average, at least 100, and preferably, about 200 or more, nucleotides before dissociation.

"Thioredoxin" is an enzyme well known to the art that is involved in oxidation and reduction reactions. It is also required as a subunit for T7 DNA polymerase activity. "Thioredoxin-independent" refers to the ability of an enzymatic activity to be active in the absence of thioredoxin.

"Promoter" is a term of art referring to sequences necessary for transcription. It does not include ribosome binding sites and other sequences primarily involved in translation.

"Gene" is a DNA sequence that contains information necessary to express a polypeptide or protein.

"Heterologous" refers herein to two DNA segments having different origins; i.e. not, in nature, being genetically or physically linked to each other. Heterologous also describes molecules that are in nature physically or genetically linked together but which are linked together in a substantially different way than is found in nature.

"Homology", as used herein, refers to the comparison of two different nucleic acid sequences. For the present purposes, assessment of homology is as a percentage of identical bases, not including gaps introduced into the sequence to achieve good alignment. Percent homology may be estimated by nucleic acid hybridization techniques, as is well understood in the art as well as by determining and comparing the exact base order of the two sequences.

"Mutation" is any change that alters the DNA or amino acid sequence. As used herein, a mutated sequence may have single or multiple changes that alter the nucleotide sequence of the DNA or the amino acid sequence of the protein. Alterations of the DNA or amino acid sequence include deletions (loss of one or more nucleotides or amino acids in the sequence), substitutions (substituting a different nucleotide or amino acid for the original nucleotide or amino acid along the sequence) and additions (addition of new nucleotides or amino acids in the original sequence).

"Purifying" refers herein to increasing the specific activity of an enzyme over the level produced in a culture in terms of units of activity per weight of protein. This term does not imply that a protein is purified to homogeneity. Purification schemes for T5-DNAP are known to the art.

"Expression" is the process by which a promoter/structural gene or promoter/nucleotide sequence produces a polypeptide. It involves transcription of the gene into messenger RNA (mRNA) and the translation of such mRNA into polypeptide(s).

"Substantially pure" means that the desired purified enzyme or polypeptide is essentially free from contaminating cellular components which are associated with the desired enzyme or polypeptide in nature. Contaminating cellular components may include, but are not limited to, phosphatases, exonucleases, endonucleases or other amino acid sequences normally associated with the desired enzyme or polypeptide.

"Origin of replication" refers to a DNA sequence from which DNA replication is begun, thereby allowing the DNA molecules which contain said origin to be maintained in a host, i.e., replicate autonomously in a host cell.

"3'-to-5' exonuclease activity" is an enzymatic activity well known to the art. This activity is often associated with DNA polymerases, and is thought to be involved in a DNA replication "editing" or correction mechanism.

"Host" is any prokaryotic or eukaryotic microorganism that is the recipient of a DNA molecule. The DNA molecule may contain, but is not limited to, a structural gene, a promoter and/or an origin of replication.

A "DNA polymerase substantially reduced in 3'-to-5' exonuclease activity" is defined herein as either (1) a mutated DNA polymerase that has about or less than 10%, or preferably about or less than 1%, of the specific activity of the corresponding unmutated, wild-type enzyme, or (2) a DNA polymerase having a 3'-to-5' exonuclease specific activity which is less than about 1 unit/mg protein, or preferably about or less than 0.1 units/mg protein. A unit of activity of 3'-to-5' exonuclease is defined as the amount of activity that solubilizes 10 nmoles of substrate ends in 60 min. at 37° C., assayed as described in the "BRL 1989 Catalogue & Reference Guide", page 5, with HhaI fragments of lambda DNA 3'-end labeled with [$^3$H]dTTP by terminal deoxynucleotidyl transferase (TdT). Protein is measured by the method of Bradford, Anal. Biochem. 72:248 (1976). As a means of comparison, natural, wild-type T5-DNAP or T5-DNAP encoded by pTTQ19-T5-2 has a specific activity of about 10 units/mg protein while the DNA polymerase encoded by pTTQ19-T5-2(Exo$^-$) has a specific activity of about 0.0001 units/mg protein, or 0.001% of the specific activity of the unmodified enzyme, a $10^5$-fold reduction.

The present invention is directed to a recombinant DNA molecule having a structural gene encoding a protein which has a processive, thioredoxin-independent DNA polymerase activity. The recombinant DNA molecule of the invention may also contain a promoter and/or an origin of replication. In this combination, the promoter and the structural gene are in such position and orientation with respect to each other that the structural gene may be expressed in a host cell under control of the promoter, and the origin of replication is capable of maintaining the promoter/structural gene/origin of replication combination in a host cell. Preferably, the promoter and the origin of replication are functional in the same host cell, exemplified herein by an E. coli host cell. The DNA molecule is preferably contained by a host cell, exemplified herein by an E. coli host cell (in particular, E. coli BH215), but may, of course, exist in vitro. The promoter may be any inducible promoter, e.g. a lambda P$_L$ promoter, a tac promoter or a lac promoter. The protein may also have a processive 3'-to-5' DNA exonuclease activity or may have substantially reduced 3'-to-5' exonuclease activity. Preferably, the structural gene is under control of a heterologous promoter. In addition, the structural gene may be under the control of a heterologous ribosome binding site, although the native T5 DNA polymerase ribosomal binding site may be used.

The structural gene should have at least about 75% homology with the native T5 DNA polymerase structural gene, and preferably at least about 90% homology, provided that the protein when expressed has T5 DNA polymerase activity. The structural gene may be derived from the T5 DNA polymerase structural gene. The DNA comprising the T5 DNA polymerase structural gene may be derived from genomic DNA, cDNA, synthetic DNA and combinations thereof. Thus, the structural gene encoding a protein of the present invention may be any gene having the desired homology and which encodes a protein with the desired activity.

Alternatively, the structural gene encodes a protein having at least about 75% homology with native T5 DNA polymerase, preferably at least about 90% homology, again provided that the protein when expressed has T5 DNA polymerase activity.

The present invention pertains both to the T5 DNA polymerase and to its functional derivatives. A "functional derivative" of T5 DNA polymerase is a molecule which possesses a biological activity (either functional or structural) that is substantially similar to a biological activity of T5 DNA polymerase. The term "functional derivative" is intended to include the "fragments," "variants," "analogues," or "chemical derivatives" of a molecule. A "fragment" of a molecule such as T5-DNAP, is meant to refer to any polypeptide subset of the molecule. A "variant" of a molecule such as T5-DNAP is meant to refer to a molecule substantially similar in structure and function to either the entire molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules is not found in the other, or if the sequence of amino acid residues is not identical. An "analogue" of a molecule such as T5-DNAP is meant to refer to a molecule substantially similar in function to either the entire molecule or to a fragment thereof. As used herein, a molecule is said to be a "chemical derivative" of another molecule when it contains additional chemical moieties not normally a part of the molecule. Such moieties may improve the molecule's solubility, absorption, biological half life, etc.

The present invention also relates to a method for production of a protein having a processive, thioredoxin-independent DNA polymerase activity having the steps of culturing a cell containing a recombinant DNA molecule under conditions where the structural gene is expressed, followed by purifying the protein expressed during the culturing step. In this method, the recombinant DNA molecule has a structural gene encoding the protein, as well as a promoter and an origin of replication. (The promoter and the structural gene are in such position and orientation with respect to each other that the promoter may regulate the expression of the gene in the cell). The origin of replication may be heterologous to the structural gene and capable of maintaining the structural gene/promoter/origin of replication combination in the host cell. Expression and maintenance are preferably in an E. coli host cell. The promoter may be heterologous to the structural gene and may be inducible, e.g. a lambda P$_L$ promoter, a tac promoter, or a lac promoter. Preferably, the structural gene is under control of a heterologous promoter. The structural gene of the invention may be under control of a heterologous ribosome binding site. The protein may have a processive 3'-to-5' DNA exonuclease activity or may have substantially reduced 3'-to-5' exonuclease activity. The structural gene may have at least about 75% homology with a T5 DNA polymerase structural gene. The structural gene may be derived from a T5 DNA polymerase structural gene. Alternatively, the structural gene encodes a protein having at least about 75% homology with T5 DNA polymerase, preferably at least about 90% homology, provided that the protein when expressed has T5-DNAP activity.

Although specific plasmids, vectors, promoters and host cells are disclosed and used in the Examples section, other promoters, vectors, and host cells, both prokaryotic and eukaryotic, are well known in the art and in keeping with the specification, may be used to practice the invention. Specific molecules exemplified herein include "clone #3", pTTQ19-T5-3, pSportT5, clone #2, pTTQ19-T5-2, and functional derivatives thereof. A functional derivative of a DNA molecule is derived from the original DNA molecule but still may express the desired structural gene in a host or in vitro, i.e., express a gene encoding for T5 DNA polymerase activity.

The present invention further relates to a protein having a processive, thioredoxin-independent DNA polymerase activity produced by the method of the present invention. This protein may have a processive 3'-to-5' DNA exonuclease activity or may have substantially reduced 3'-to-5' exonuclease activity. The protein should have at least about 75% homology with T5 DNA polymerase, and preferably at least about 90% homology, provided that the T5-DNAP has biological activity. The protein may be derived from, and is herein exemplified by, T5 DNA polymerase. Standard protein purification techniques well known in the art may be used to purify the polymerase proteins of the present invention.

The T5 DNA polymerase of this invention may be used in cloning and in vitro gene expression experiments to produce heterologous polypeptides from the cloned genes. The T5-DNAP of this invention may also be used for DNA sequencing, DNA labeling, and amplification reactions.

Having now generally described this invention, the same will be better understood by reference to specific examples, which are included herein for purposes of illustration only, and are not intended to be limiting unless otherwise specified.

EXAMPLES

Though the written description that follows is complete and accurate, some may find that overall cloning strategy may be more easily understood by reference to FIGS. 2–6, and 9.

Example 1: Isolation of T5 phage DNA

Growth of E. coli and infection with bacteriophage T5 were done as previously described by Schneider SE et al., J. Virol. 56:245–249 (1985).

Purification of T5 phage DNA was isolated by the following procedure. Briefly, E. coli F (provided by Dr. Robert K. Fujimura, Oak Ridge National Laboratory, Oak Ridge, Tenn.) was grown in Luria broth at 37° C. to an O.D.550 nm of about 0.50. $CaCl_2$ was added to a final concentration of 2 mM. T5 phage (nick-less) (provided by Dr. Fujimura) was added at an approximate cell:phage ratio of 15:0.16. The phage-infected cells were shaken very slowly at 37° C. until the O.D.550 decreased from about 0.50 to about 0.2. The cells and the cell debris were removed by centrifugation. The supernatant was saved.

To about 900 ml of this supernatant, DNase I and RNase A were added to final concentrations of 10 μg/ml each and $MgCl_2$ was added at a final concentration of 5 mM. The supernatant was then incubated 30 minutes at room temperature. Solid NaCl was added to 1M and dissolved. Then PEG 6000–8000 (PEG=polyethylene glycol) was added to 10% and dissolved. The mixture was incubated overnight at 4° C. The resultant solution of phage was centrifuged for 15 minutes at 6000 rpm; suspended in 50 ml buffer D (buffer D=50 mM Tris-HCl, pH 7.2, 8.5 mM NaCl, 1 mM $MgCl_2$ and 0.1 mM $CaCl_2$).

A portion (25 ml) was mixed slowly with 20 ml chloroform and then centrifuged for 10 minutes. The aqueous, DNA-containing layer (20 ml) was recovered and diluted to 40 ml with 20 ml of buffer D. SDS (sodium dodecyl sulfate) was added to this layer to a concentration of 1%. After mixing slowly, this was incubated at 37° C. for 10 minutes. Water-saturated phenol (25 ml) was added, mixed slowly but thoroughly and then centrifuged to separate the layers. The upper, viscous, DNA-containing layer was removed carefully and extracted once again with phenol. Then an equal volume of water-saturated phenol:$CHCl_3$:isoamyl alcohol (50:48:2 v:v:v) was added, mixed slowly and centrifuged to separate the layer. The DNA-containing viscous layer was removed and an equal volume of buffer D was added.

CsCl was added to 1.15 g/ml for purification of the phage DNA by CsCl gradient centrifugation at 40,000 r.p.m. for 2 days. About 9.6 mg of T5 DNA was recovered in 15 ml volume.

Example 2: Exonuclease III and S1 nuclease digestion

Figure 2A:
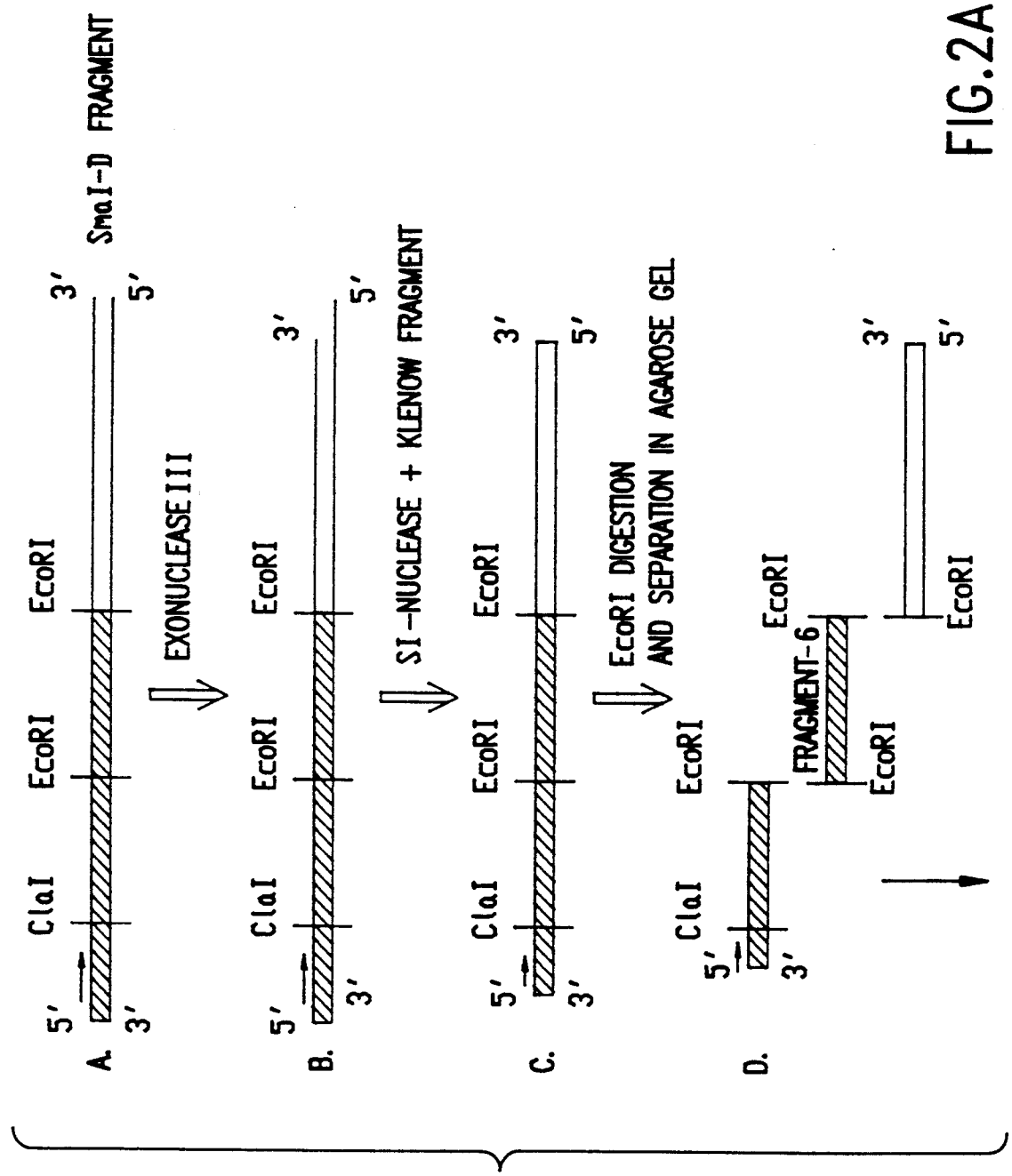
FIGS. 2A, 2B, and 2C are schematic drawings not necessarily to scale, of many of the cloning schemes described in the Examples, and is especially useful in understanding Examples 2 through 6. Plasmid pTTQ19-T5-3 utilizes the TTG position −78 of Leavitt & Ito (supra) as its initiation codon, while plasmid pTTQ19-T5-2 uses the ATG at position +12 as its start codon.
Figure 2B:
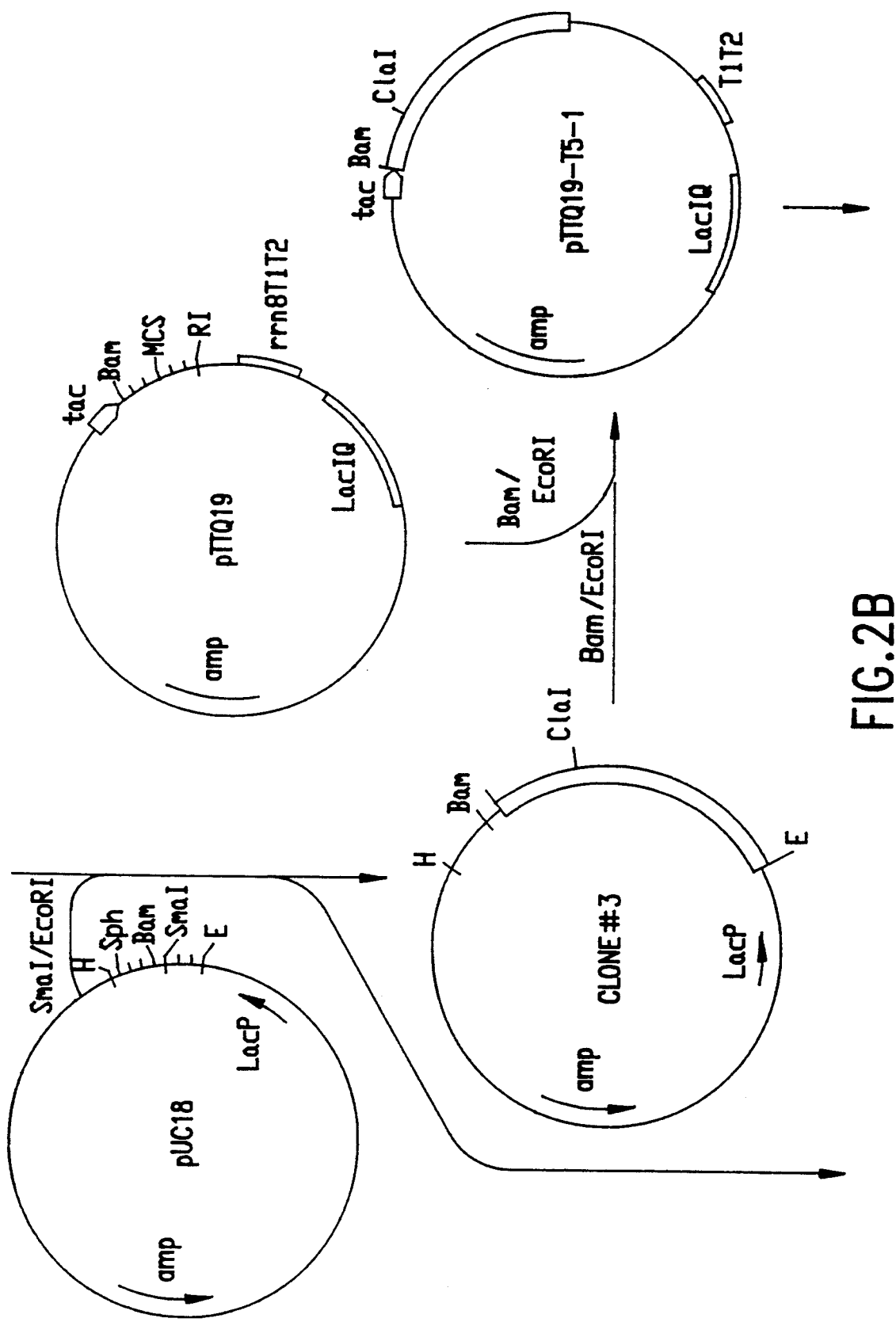
Figure 2C:
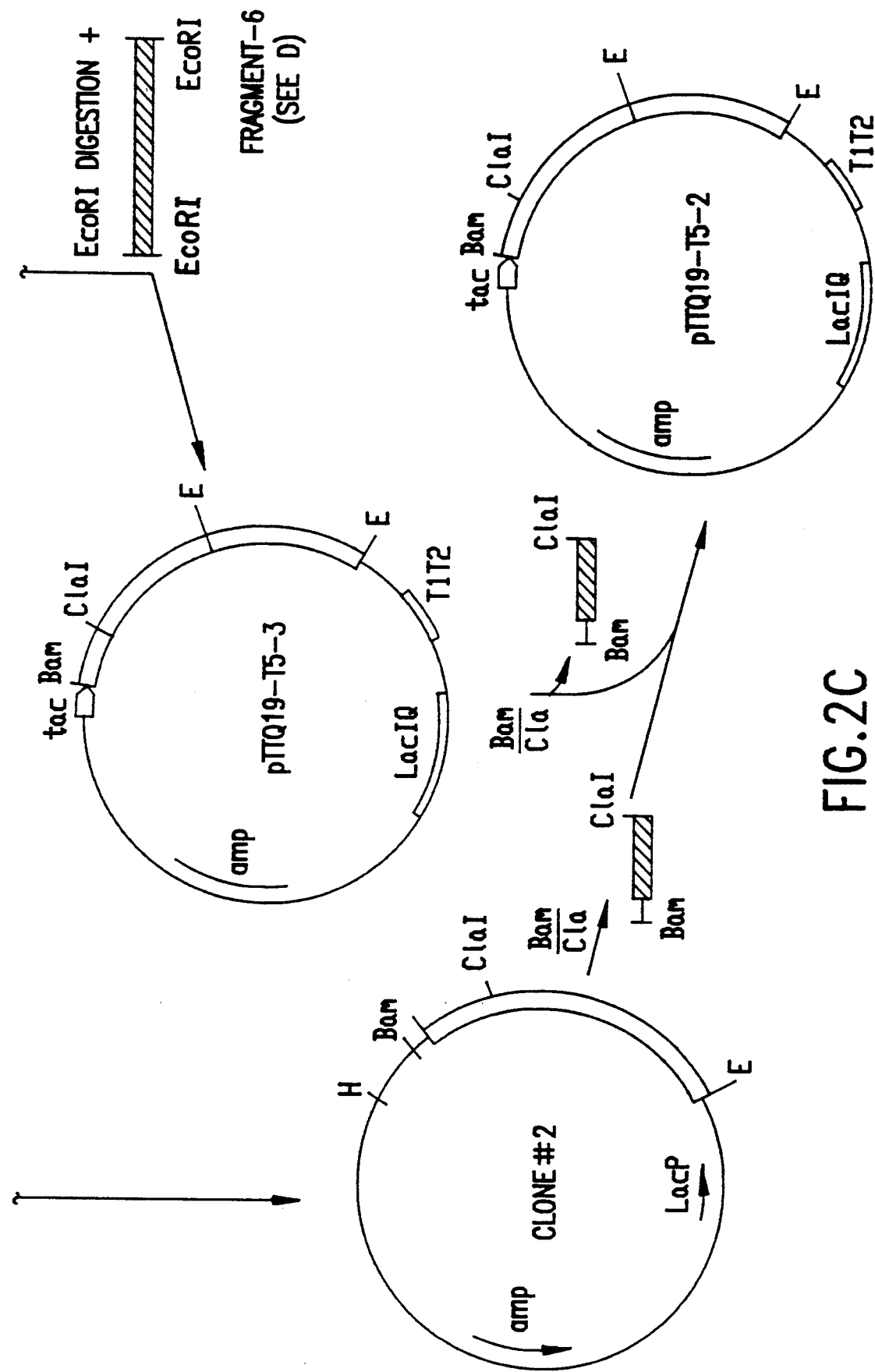

Initial attempts to clone an intact fragment containing the polymerase gene met with failure. In addition, smaller fragments containing a portion of polymerase gene (5'-end) and the upstream region also could not be cloned. This suggested that the upstream region of the T5-DNAP gene contained either a very strong (e.g. constitutive) promoter or some other sequence(s) lethal to E. coli. Therefore, upstream sequences were deleted as follows. A fragment containing the entire T5-DNAP gene was generated by SmaI digestion and isolated (FIG. 2, DNA A.). Terminal sequences were then removed from that fragment by treating with exonuclease III (FIG. 2, DNA B.), which removes a single strand of a DNA duplex, attacking from the 3'-ends, and S1 nuclease, which removed single-stranded ends left after exonuclease III treatment. The ends were "polished" with the Klenow fragment of DNA polymerase I in the presence of all four deoxyribonucleotide triphosphates (FIG. 2, DNA C.). The resulting blunt-ended fragment was then digested with EcoRI to facilitate later cloning (FIG. 2, DNA D.). The following details the above described steps.

SmaI digestion produces four large fragments, the smallest (about 12 kilobase pairs (kbp)) of which has been suggested (Fujimura R et al., J. Virol. 53:495–500 (1985)) to contain the intact polymerase gene. Therefore, the smallest SmaI fragment was purified from agarose gels with Gene-Clean ™ kits (Bio 101, P.O. Box 2284, La Jolla, Calif. 92038-2284 USA).

Exonuclease III (320 units) was added to approximately 2.5 μg DNA in 100 μl of buffer (50 mM Tris-HCl, pH 8.0, 10 mM $MgCl_2$ and 1 mM DTT (DTT=dithiothreitol) and incubated at 37° C. At various times aliquots were removed. Each aliquot was placed in its own tube containing 200 mM NaCl, 50 mM EDTA (EDTA=ethylenediamine tetraacetic acid). The tubes were then heated at 70° C. for 10 minutes. The DNA contained therein was ethanol precipitated by addition of 0.1 volume of 3M sodium acetate, pH 6.0, and 2 volumes of ethanol, followed by incubation in dry ice for 1 to 2 minutes. The DNA precipitate was collected by centrifugation for 30 minutes at 14,000 r.p.m. in an Eppendorf microfuge.

The exonuclease III digested DNA was dissolved in 50 μl of S1 nuclease buffer (30 mM sodium acetate, pH 4.6, 50 mM NaCl, 1 mM zinc acetate, and 9 units of S1 nuclease). The reaction was incubated for 30 minutes at room temperature. After extraction with an equal volume of phenol:$CHCl_3$:isoamyl alcohol, the DNA was ethanol precipitated as described above.

The S1 nuclease treated DNA was redissolved in 30 μl of a buffer containing 50 mM potassium phosphate, pH 7.5, 3 mM $MgCl_2$, 2 mM DTT, 0.1 mM each of dATP, dTTP, dGTP, and dCTP, and 1 unit of the Klenow fragment of *E. coli* DNA polymerase I. The reaction was incubated at room temperature for 5 minutes, extracted with phenol:CHCl3:isoamyl alcohol, and ethanol precipitated as above.

EcoRI cleaves the SmaI fragment isolated above in two places, thereby generating three fragments. The terminally deleted SmaI DNA fragment was digested with EcoRI and the resulting DNA fragments were separated by agarose gel electrophoresis and the bands around 2600 base pairs (bp) in size were isolated from the agarose gel by the Gene-Clean TM method. These bands of about 2.6 kbp (kilobase pairs) contained two fragments. One fragment was the central of the three EcoRI subfragments of the terminally digested SmaI fragment, the other fragment was the shorter of the two end fragments. This end fragment had had its SmaI end trimmed by the exonuclease III/S1 nuclease treatment and had a ClaI site proximal to the "SmaI" end and distal to its EcoRI end. This ClaI site was useful for orienting the fragment, being at the 5'-end of the fragment as defined by the orientation of the T5-DNAP gene.

Example 3: Cloning of a fragment including 5'-flanking sequences

S1 nuclease and Klenow fragment treatment of exonuclease III treated DNA had produced a blunt-ended fragment. Later, EcoRI treatment resulted in a fragment of around 2.6 kbp having a blunt-end on one side (the "SmaI" end, 5'-to the T5-DNAP gene) and sticky EcoRI end on the other. This purified fragment was mixed with, ligated to, and to cloned into pUC18 DNA (Yanisch-Perron C et al., Gene 33:103–119 (1985)) which had been previously digested with SmaI and EcoRI. (Note that though the 2.6 kbp band contained two different fragments, the 2.6 kbp "end" fragment was preferentially cloned because the internal fragment lacked a blunt end, i.e. its ends did not match those of the vector.) This cloning operation destroyed the SmaI site but preserved the EcoRI site. Six different clones having inserts of varying lengths (but all are around 2.6 kbp) were isolated. One of them, labeled #3, was chosen for further work because this clone contained the largest fragment, i.e. the smallest deletion. DNA sequencing showed that the T5 sequences of clone #3 started at nucleotide −98 in the sequence of Leavitt & Ito, supra.

pTTQ19 DNA (Stark MJR, Gene 51:255–267 (1987); available from Amersham, International, plc) was digested with BamHI and EcoRI and then mixed with and ligated to the 2.6 kbp BamHI/EcoRI fragment of clone #3. The BamHI site was present (in the multiple cloning site (polylinker) of pUC18) next to the SmaI site which had been used to clone the 2.6 kbp fragment of clone #3. The resulting clone was reopened with EcoRI and mixed with and ligated to T5 EcoRI fragment 6 in order to introduce any missing 3'-end (carboxyl-terminus encoding end) of T5 polymerase gene. (Note that EcoRI fragment 6 can be isolated free of other T5 sequences, the mixture of two 2.6 kbp fragments was due to an additional cleavage with SmaI.) The resultant clone, pTTQ19-T5-3, produced significant amounts of polymerase activity only after induction with IPTG. As discussed in Example 12, pTTQ19-T5-3 containing cells produced full length T5 DNA polymerase.

Example 4: Optimization of the 5'-end of the T5-DNAP gene

Clone #3 was selected from among other clones made at the same time because it had the smallest deletion of those screened. Sequencing of the 5'-end region of clone #3 and comparison with the published sequence (Leavitt & Ito, supra) showed that the T5 DNA insert of clone #3 carried a promoter-like sequence and a ribosome-binding-site. Apparently, however, the promoter-like sequence is not functional; rather, its presence reduces production of T5-DNAP from the tac promoter. Therefore, larger deletions were introduced into pTTQ19-T5-3 to test their effect on enzyme production. However, as discussed in Example 12, these deletions actually removed part of the N-terminal region of the T5 DNA polymerase gene, although the resulting truncated clones expressed active protein.

The 5'-end of the clone #3 T5 DNA was removed from pTTQ19-T5-3 by digestion with BamHI and ClaI. BamHI/ClaI fragments from independently derived clones, produced in the same experiment that produced clone #3, individually were mixed with and ligated to aliquots of this DNA. Transformants containing the resultant clones were screened for T5-DNAP production; larger deletions were observed to produce more enzyme. The clone which produced the highest level of T5-DNAP was estimated by gel electrophoretic analysis to lack all of the presumptive promoter region and the presumptive ribosome binding site. DNA sequencing confirmed that, the 5'-end of the truncated T5 DNA polymerases structural gene is at nucleotide +12, as numbered by Leavitt & Ito, supra. This clone, labeled pTTQ19-T5-2, produced about 8 times more enzymatic activity than pTTQ19-T5-3; cells harboring this plasmid made about 12-fold more enzyme than virus-infected cells. However, as discussed in Example 12, it has been found that the majority of this truncated protein was insoluble and formed inclusion bodies in the cell.

*E. coli* BH215 (pTTQ19-T5-2) was deposited under the Budapest Treaty with an International Depository Authority, the Patent Culture Collection, Northern Regional Research Center, USDA, 1815 N. University St., Peoria, Ill. 61604 USA, as NRRL B-18526. Availability of this material is not necessary for practice of the present invention, which may be performed using the teachings of the present disclosure in combination with publicly available materials and information and techniques well known in the arts of molecular biology, recombinant DNA, and chimeric gene expression. This strain is best maintained on Luria broth supplemented with 100 mg/l ampicillin and 0.2% glucose, to fully repress the tac promoter (see Stark, supra), at 30° C., which lowers the copy number of pUC-based plasmids, thereby lowering the chances of picking up a mutation.

Although a plasmid containing the full length T5 DNA polymerase structural gene was not deposited, it will be apparent to those of skill in the art that full length clones can easily be obtained given the disclosure of this application.

Example 5: Miscellaneous experiments

Thioredoxin is necessary for production of T5 phage; an *E. coli* mutant deficient for thioredoxin did not support growth of T5 while an isogeneic strain did. In contrast, active T5-DNAP is made in the deficient strain if it harbors a clone that can express T5-DNAP. Furthermore, addition of thioredoxin in reactions containing T5-DNAP made in a thioredoxin-deficient strain did not affect activity. Therefore, thioredoxin is not an accessory protein to the polymerase and has some other function in the T5 life cycle.

The BamHI/ClaI fragment of clone #3 was subcloned as a BamHI-blunt fragment by treating ClaI-digested DNA with Klenow fragment and then digesting with BamHI into M13mp18 and M13mp19 at BamHI/SmaI sites, which are identical except for the orientation of their poly-linkers (Yanisch-Perron et al., supra). This fragment, about 650 bp in length, has the pUC18 poly-linker BamHI site at one end and the T5 ClaI site present near the "5-end" of the 2.6 kbp "end fragment" at the other end. More than 300 times more clones were observed with the M13mp18 vector, where the T5 fragment was in the opposite orientation to be transcribed by the lac promoter of the pUC vector, than with M13mp19, where it is the correct orientation. The BamHI/ClaI fragment represents the amino-terminal end of T5 DNAP protein and the 3'-to-5' exonucleases of several DNA polymerases are known to be present in the amino-terminal region. Therefore, it is likely that this region of the T5-DNAP gene encodes the 3'-to-5' exonuclease activity, thus suggesting that expression of this activity in the absence of the polymerase activity may be detrimental to E. coli.

Example 6: Cloning of 5'-end of structural gene of T5-DNAP

Figure 3:
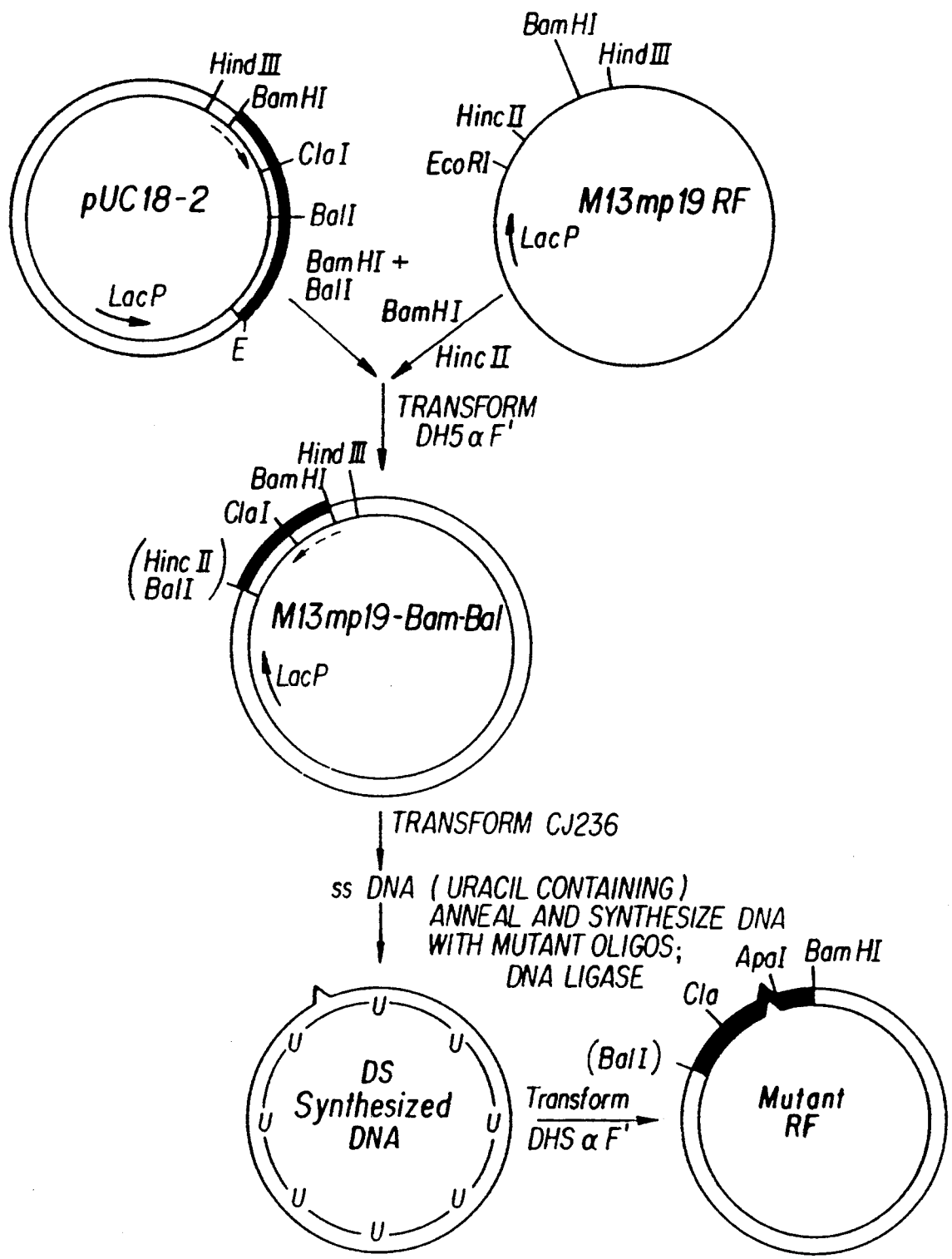
FIG. 3 is a schematic drawing, not necessarily to scale, of the preparation of a "mutant RF" (Example 6, see also Example 8).

A BamHI/BalI fragment about 850 bp in length, was sub-cloned into M13mp19 as follows. About 1 μg of clone #2 (FIG. 2) DNA was digested with BamHI and BalI. The approximately 850 bp fragment was purified from an agarose gel after electrophoresis by a Gene Clean ™ Kit (Bio101, P.O. Box 2284, La Jolla, Calif. 92038). About 1 μg of M13mp19 DNA was digested with BamHI and HincII and ligated with 850 bp BamHI/BalI fragment. The result of this operation was that the fragment was cloned in a translational polarity opposite to the polarity of the lac promoter present in the M13mp19 vector (FIG. 3). Therefore, expression of cloned gene product was eliminated. Cloning of a BamHI/ClaI fragment of T5-DNAP gene in the same polarity as the lac promoter was found to be deleterious for the cell (see Example 5). This implied that the exonuclease domain may be present in the amino-terminal end of the protein or 5'-end of the gene. The ligated DNA was introduced into E. coli DH5 αF' cells by a standard method. Clones containing the fragments were selected and phage stocks of the desired clones were saved as described by BioRad's Muta-Gene ™ M13 in vitro mutagenesis kit (BioRad Laboratories, 1414 Harbour Way South, Richmond, Calif. 94804). Uracil-containing single-stranded DNA (ssDNA) was isolated from dut⁻ ung⁻ CJ236 host cells by the method described in the kit.

Example 7: Design of a primer for in vitro mutagenesis

As explained in Examples 5 and 6, the 3'-to-5' exonuclease domain of T5-DNAP probably was at the 5'-end of the structural gene. Site of mutagenesis within this region was chosen by analogy with the E. coli DNA polymerase I. T5-DNAP was suggested to be highly related to E. coli DNA polymerase I, (Leavitt MC & Ito J, Proc. Natl. Acad. Sci. USA 86:4465–4469 (1989)).

The amino acids Asp$^{355}$ and Glu$^{357}$ of E. coli DNA polymerase I and Asp$^{138}$ and Glu$^{140}$ of T5-DNAP in the sequence of Leavitt & Ito, supra, are conserved. The amino acids Asp$^{355}$ and Glu$^{357}$ of E. coli DNA polymerase I were suggested to be involved in 3'-to-5' exonuclease activity by Joyce CM & Steitz TA (Trends Biochem. Sci. 12:288–292 (1987)). Similar conserved amino acids between E. coli DNA polymerase I and T7 DNA polymerase were also found (Leavitt and Ito, supra; Johnson et al., 8th Summer Symposium in Molecular Biology, "DNA protein interaction", Penn. St. Univ., Jul. 26–28, 1989). Johnson et al. showed that changing of Asp$^5$ and Glu$^7$ of T7 DNA polymerase to Ala$^5$ and Ala$^7$ resulted in the reduction of 3'-to-5' exonuclease activity 10$^4$-fold relative to native T7 DNA polymerase. Tabor S & Richardson CC (J. Biol. Chem. 264:6447–4658 (1989)), on the other hand, showed that deletion of Ser$^{122}$ and His$^{123}$ of T7 DNA polymerase reduced the 3'-to-5' exonuclease activity to less than 0.001% of the activity of native T7 DNA polymerase. Results of Johnson et al. and of Tabor and Richardson suggest that the exonuclease domain is in the 5'-end of the gene, however, mutation in two different locations resulted in loss of 3'-to-5' exonuclease activity. Therefore, a mutation was made in the T5-DNAP based upon the analogy with both E. coli DNA polymerase I and T7 DNA polymerase (i.e. changing Asp$^{138}$ and Glu$^{140}$ in the T5-DNAP protein, as numbered by Leavitt and Ito, supra). Therefore, an oligonucleotide with the following sequence [SEQ ID NO: 1] was made by using standard techniques:

5' G GTT ATC GGG CCC GTC GCA TTC GCC TCC GCA ACC TCA GCA C 3'

(Underlined bases indicate substitutions relative to the native sequences and spaces delineate the polypeptide-encoding codons.) This oligonucleotide changes the native Asp$^{138}$ and the native Glu$^{140}$ to Ala$^{138}$ and Ala$^{140}$, respectively. The sequence 5'GGGCCC3' was introduced into this oligonucleotide without changing the encoded amino acid. This aided identification of mutant DNA by formation of an easily screenable ApaI site.

The oligonucleotide designed above was synthesized by standard methods and was phosphorylated by T4 polynucleotide kinase.

Example 8: In vitro mutagenesis of T5-DNAP

The uracil-containing ssDNA isolated in Example 6 was annealed with the oligonucleotide designed and prepared in Example 7. The oligonucleotide/ssDNA complex was polymerized using T4 DNA polymerase and T4 DNA ligase in the presence of all four deoxyribonucleotides using BioRad Muta-Gene ™ kit. The synthesized DNA was introduced into E. coli DH5 α F' cells. The clones with mutant oligonucleotides were screened for the presence of ApaI site. Clones that contained an ApaI site were presumed to be mutant clones. Mutant clones derived from each oligonucleotide were pooled to form a "mutant RF" (FIG. 3).

Example 9: Introduction of mutant fragment into pTTQ19-T5-2

Figure 4:
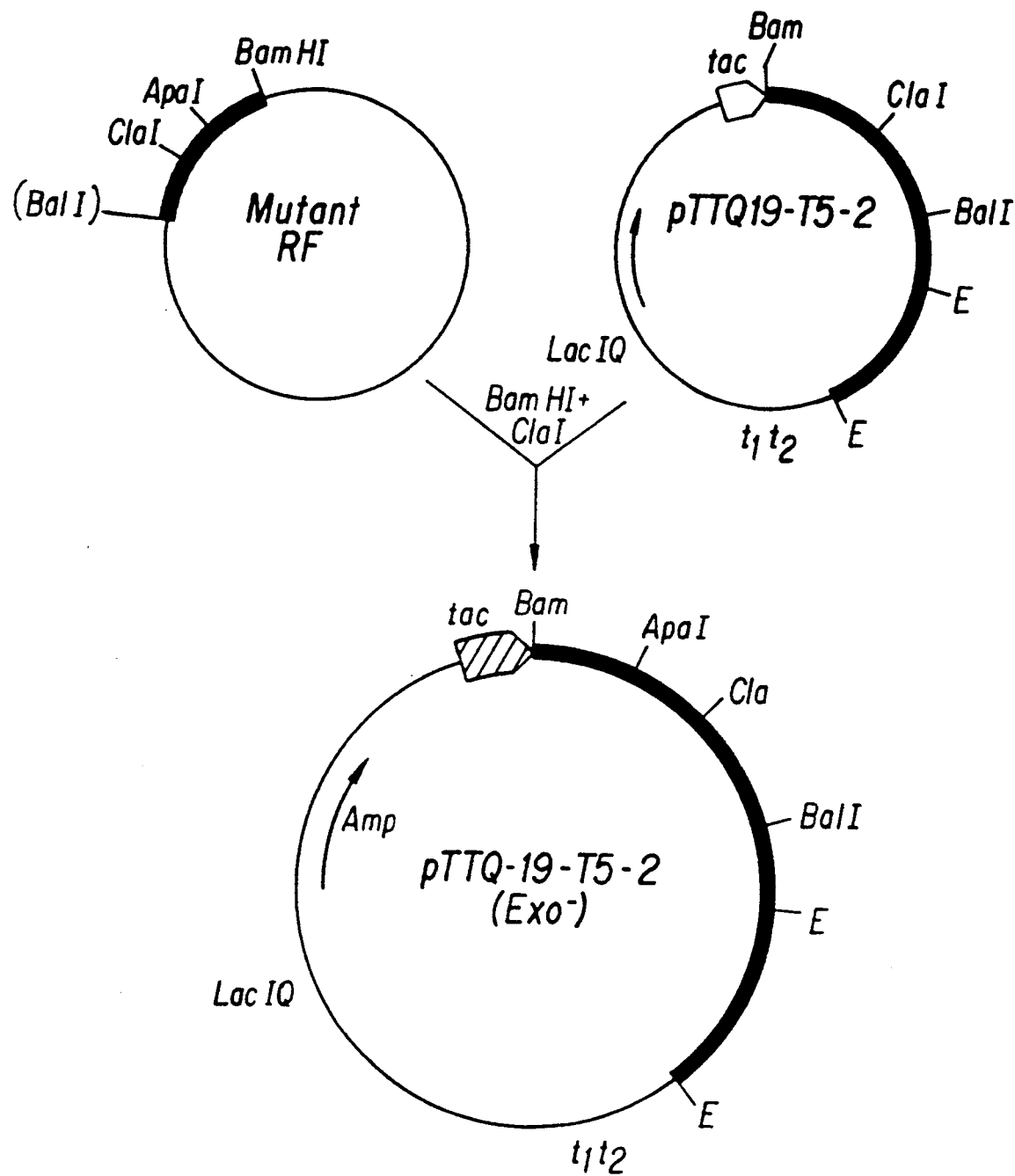
FIG. 4 is a schematic drawing, not necessarily to scale, of pTTQ19-T5-2(Exo−) (Example 9). This plasmid uses the ATG at position +12 of Leavitt & Ito supra as its initiation codon.

BamHI/ClaI digestion of mutant RF (FIG. 4) generates 4 fragments. The smallest (about 500 bp) of these fragments contains the mutated sequence having an ApaI site. This fragment was purified from an agarose gel as described in Example 2. pTTQ19-T5-2 DNA was digested with BamHI and ClaI and the smallest fragment was replaced by the BamHI-ClaI fragments of the mutant RF (FIG. 4). The correct assembly of the resulting DNA construction was verified by checking for the presence of an ApaI site between the BamHI and ClaI sites. Several cell lines containing plasmids with the mutant fragment were assayed for polymerase and 3'-to-5' exonuclease activities. A plasmid having a properly inserted mutation and expressing T5 DNA polymerase activity was designated pTTQ19-T5-2(Exo−).

Example 10: Placement of T5-DNAP genes behind lambda promoters

Placement the T5-DNAP gene under control of a bacteriophage lambda $P_L$ promoter took advantage of NdeI sites covering the ATG translational start sites of the T5-DNAP and T5-DNAP-Exo− genes and an NdeI site after the lambda $P_L$ promoter of pKD1 (Kotewicz M et al., Gene 35:249-259 (1985)).

Figure 5:
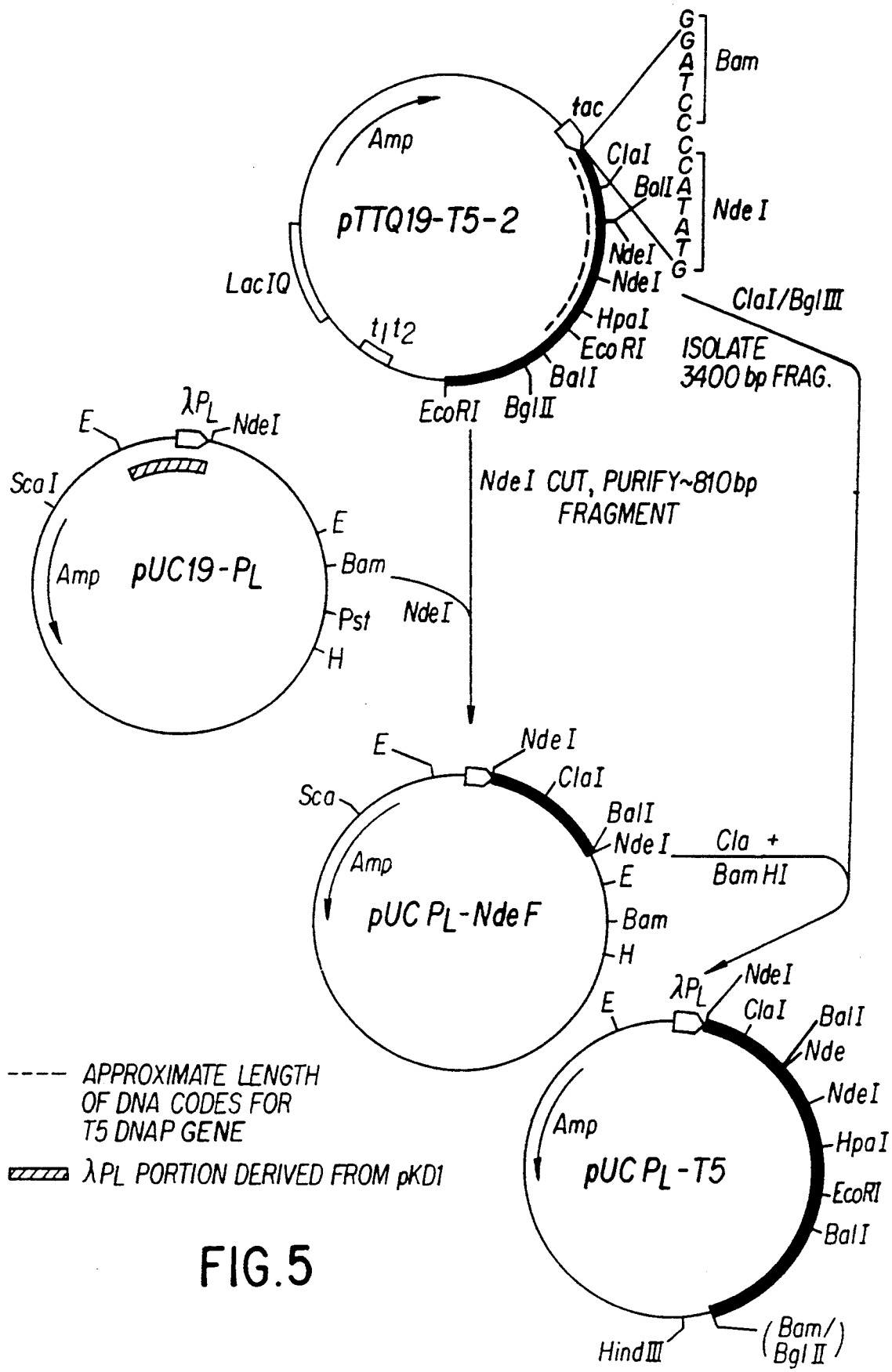
FIG. 5 is a schematic drawing, not necessarily to scale, of a construction having the T5-DNAP gene under control of the lambda P$_L$ promoter (Example 10).
Figure 6:
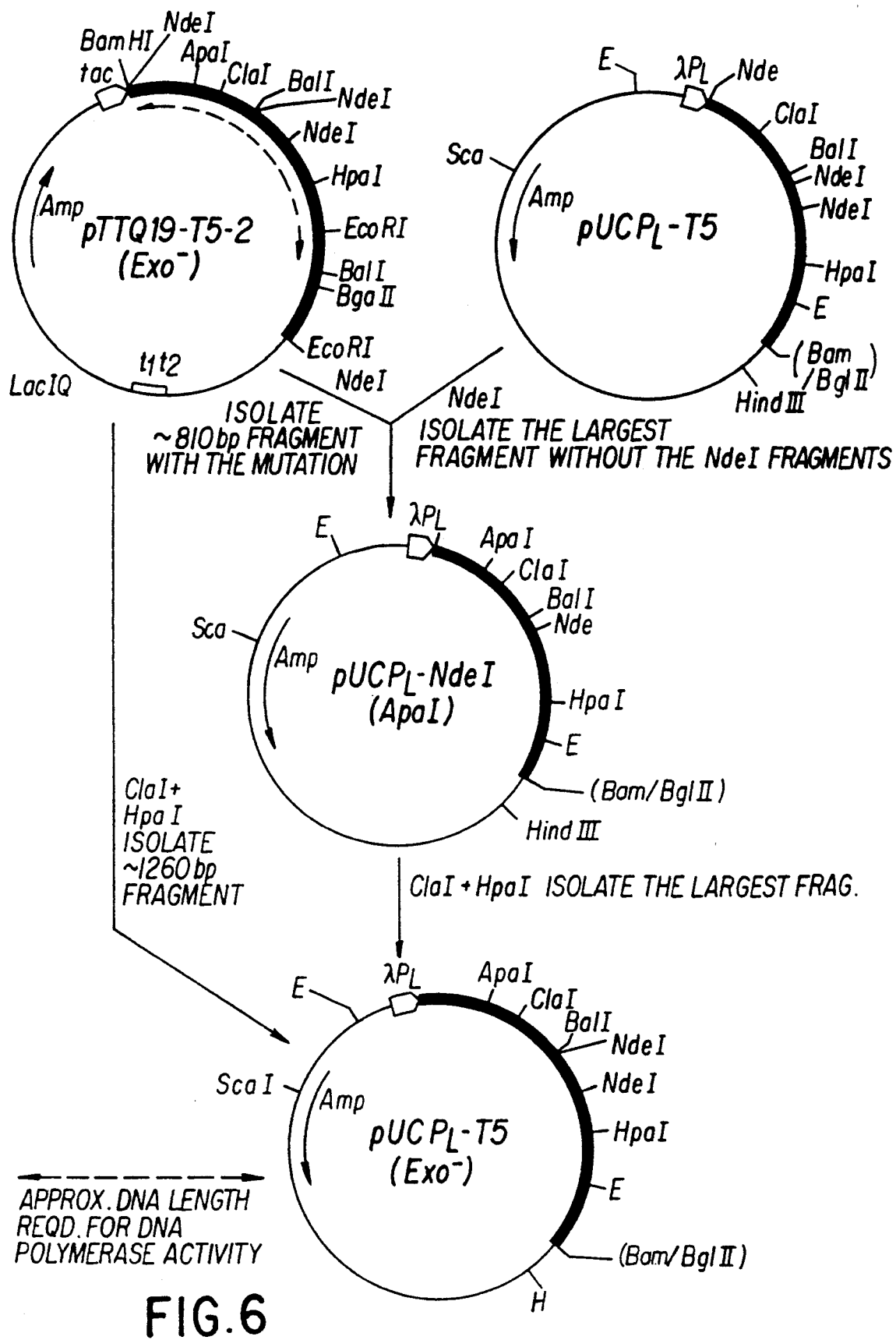
FIG. 6 is a schematic diagram, not necessarily to scale, of the construction of an exonuclease deficient mutant of T5 DNAP under control of the lambda P$_L$ promoter (Example 10).

A 0.81 kbp fragment was isolated from NdeI-cut pTTQ19-T5-2. This fragment, which carried a 5'-portion of the T5-DNAP structural gene, was mixed with and ligated to NdeI-linearized pUC19-$P_L$. Proper orientation of the resultant plasmid, pUCP$_L$-NdeF, was verified by relative positions of the BalI site of the insert and the BamHI site of the vector. pUCP$_L$-NdeF DNA was cut with BamHI and ClaI and then mixed with and ligated to a purified, 3.4 kbp ClaI/BglII fragment of pTTQ19-T5-2, which carried a 3'-portion of the T5-DNAP structural gene. The resultant plasmid, pUCP$_L$-T5, had a complete T5-DNAP structural gene expressible under control of a lambda $P_L$ promoter (FIG. 5).

pUCP$_L$-T5 DNA was digested with NdeI and the largest fragment, which lacked a 5'-portion of the T5-DNAP structural gene, was isolated. pTTQ19-T5-2(Exo−) was digested with NdeI and a 0.81 kbp fragment, carrying a 5'-portion of the mutated T5-DNAP gene, was isolated. These two fragments were mixed with each other and ligated to form pUCP$_L$-NdeI(ApaI), which lacked a central portion of the T5-DNAP structural gene. This plasmid was cut with ClaI and HpaI and the largest fragment, deleted for a central portion of the T5-DNAP gene, was isolated. This fragment was mixed with and ligated to a 1.26 kbp ClaI/HpaI fragment of pTTQ19-T5-2(Exo−). The resulting plasmid, pUCP$_L$-T5(Exo−), carried a complete T5-DNAP-Exo− structural gene under control of a lambda $P_L$ promoter (FIG. 6).

Example 11: 3'-to-5' exonuclease activity in the mutant protein

T5 DNA polymerase purified from E. coli cells containing either pTTQ19-T5-2-Exo− or pUCP$_L$-T5(Exo−) exhibited about $10^5$-fold less 3'-to-5' exonuclease activity compared to native T5 DNA polymerase isolated from phage infected cells or from cells harboring the plasmid pTTQ19-T5-2. 3'-to-5' exonuclease activity was determined by the procedure described above in the Detailed Description of the Invention in the definition of "DNA polymerase substantially reduced in 3'-to-5' exonuclease activity". Unmodified T5 DNAP has a 3'-to-5' exonuclease specific activity of about 10 units/mg protein. In contrast, the mutated DNA polymerase of the present invention had a 3'-to-5' specific activity of $1 \times 10^{-4}$ units/mg protein.

Example 12: Cloning and Expression of Full Length T5 DNA Polymerase

Clones pUCP$_L$-T5 and pTTQ-T5-2 produced T5 DNA polymerase which comprised more than 40% of the total cellular protein. However, the majority of the polymerase produced by cells containing these plasmids was insoluble as inclusion bodies. In addition, purified T5 DNA polymerase from these clones was smaller than the T5 DNA polymerase isolated from T5 phage infected cells. Initially, it was presumed that the size variation was due to proteolytic cleavage, even though the T5 DNA polymerase proteins produced by these clones retained full polymerase activity.

The constructs described above contain the ATG initiation codon (nucleotide+12 of Levitt & Ito, supra), a lambda $P_L$ promoter, and a lambda cII ribosome binding site (for pUCP$_L$-T5) or tac promoter and lac ribosome-binding-site (for pTTQ19-T5-2).

A careful examination of the DNA sequence of the T5 DNA polymerase gene revealed that the ribosome binding site (RBS) suggested by Leavitt & Ito is 17 nucleotides upstream of the initiation codon ATG (nucleotide+12 of the sequence published by Leavitt & Ito within the NdeI site). Most of the ribosome binding sites are centered some 6-13 nucleotides upstream of the initiation codon. Since the distance in the above Examples is unusual, 17 nucleotides as opposed to 6-13 nucleotides, Applicant looked for another possible ribosome binding site. Applicant detected a putative ribosome-binding-site 5'AGGAG3' starting at nucleotide −90 of Leavitt & Ito, supra. This putative ribosome-binding-site is followed by a rare TTG initiation codon at nucleotide −78 (see p. 13 in M. Kozak Microbiol. Rev. 47:1-47 (1983)). Even though ATG and GTG are the preferred initiation codons, TTG is also used rarely as an initiation codon in E. coli. If this is the case, then the previous T5 DNA polymerase isolated from the constructs initiated from the codon ATG (nucleotide+12 of Leavitt & Ito's published sequence) were actually a truncated form (though active), because the ATG is in the same reading frame with the TTG. Thus, the smaller form appeared not to be a proteolytic cleavage product, but rather a truncated form of the T5 DNA polymerase protein due to the loss of some of the N-terminal region of the wild-type structural gene.

To confirm that the TTG codon located at position −78 of Leavitt & Ito is the initiation codon, clone #3 was used as a source to obtain the structural gene having the TTG initiation codon. The sequence of clone #3 starts at nucleotide −98 in the sequence published by Leavitt & Ito and contains the predicted ribosome-binding-site and the TTG initiation codon. The TTG initiation codon is shown at position 152 in FIG. 8. In addition, the beginning of the T5 DNA sequence contained by clone #3 is at position 132 in FIG. 8. Thus, clone #3 contains the RBS and TTG initiation codon of T5 DNA polymerase.

To reconstitute the entire T5 DNA polymerase gene the EcoRI fragment 6 (EcoRI-6) was introduced at the EcoRI site of clone #3. There is a BglII site within the EcoRI-6 fragment but outside the T5-DNA polymerase gene. Therefore, the BamHI-BglII fragment containing the entire T5 DNA polymerase gene was cloned at the BamHI site of pSPORT 1 (available commercially from Life Technologies, Inc.). The resulting clone was called pSportT5 and FIG. 9 shows the cloning scheme used to construct pSportT5. Clones containing the fragment in both orientations with respect to the lac promoter were tested for T5 DNA polymerase activity in the induced (with IPTG) and uninduced conditions. Only clones with the correct orientation (pSportT5) with respect to the lac promoter produced T5 DNA polymerase. The amount of T5 DNA polymerase produced after induction is about 2-5%. However, the produced T5 DNA polymerase was soluble and no inclusion bodies were detected. Plasmid pTTQ19-T5-3 also produced full length T5 DNA polymerase, although expression is controlled by the tac promoter. Expression of T5 DNA polymerase of pSportT5 is controlled by a lac promoter.

Purified T5 DNA polymerase from this new construct was analyzed in comparison with the smaller T5 DNA polymerase (produced from the previous clones) and T5 DNA polymerase isolated from the T5 phage infected cells. Western analysis showed that the T5 DNA polymerase from the present clone and T5 phage infected cells migrated identically in the polyacrylamide gel, while T5 DNA polymerase isolated from the previous clone migrated faster in the same gel.

The amino terminal sequence analysis of purified T5 DNA polymerase protein isolated from the present clone showed the sequence to be [SEQ ID NO: 2]

Met-Lys-Ile-Ala-Val-Val-Asp-Lys-Ala-Leu, which is consistent with the prediction that TTG is the initiation codon for full length T5 DNA polymerase.

Applicant has also demonstrated that the T5 DNA polymerase from another clone (clone #7), which starts at nucleotide −60 of the sequence published by Leavitt & Ito (see FIG. 8), cannot be expressed when placed under similar lac promoter control. This particular clone lacks both initiation codon (TTG) and the ribosome-binding site. This clone however, contains Leavitt & Ito suggested ribosome binding site and the ATG initiation codon. Failure to produce active T5 DNA polymerase suggests that the ribosome-binding site suggested by Leavitt & Ito cannot be an actual ribosome binding site. This construct could only produce a truncated T5 DNA polymerase protein if the ribosome binding site suggested by Leavitt & Ito was the correct RBS.

These data confirm three points. (1) The initiation codon of T5 DNA polymerase is the TTG present at nucleotide −78 of the sequence published by Leavitt & Ito and the ribosome-binding-site starting at −90. (2) The T5 DNA polymerase purified from the previous clone is in fact a truncated, but active, form of intact T5 DNA polymerase. (3) The truncated T5 DNA polymerase is missing 30 amino acids from the N-terminal region. Thus, full length T5 DNA polymerase is 30 amino acids longer than the truncated form (see FIG. 7).

Example 13: Introduction of Mutant Fragment Into pSportT5

To construct a mutant of the full length T5 DNA polymerase to produce a protein which is substantially reduced in 3'-to-5' exonuclease activity, a BspEI/ClaI fragment (approximately 650 base pairs) was isolated from plasmid pUCP$_L$-T5 (Exo−). This BspEI/ClaI fragment of pUCP$_L$-T5 (Exo−) contains the mutated sequence in the 3' to 5' exonuclease domain of T5 DNA polymerase as described in Example 7. The wild-type BspEI/ClaI fragment of clone #3 was replaced by the mutated fragment using standard recombinant DNA techniques producing a plasmid called clone #3/ApaI. Finally, the wild-type BamHI/ClaI fragment of pSportT5 was replaced with the mutated BamHI/ClaI fragment derived from the clone #3/ApaI plasmid. The resulting plasmid, encoding a full length T5 DNA polymerase protein substantially reduced in 3'-to-5' exonuclease activity, was called pSportT5E. As noted above, plasmid pTTQ19-T5-3 produces full length T5 DNA polymerase. Using the procedure in this Example, PTTQ19-T5-3 may also be mutated to produce a full length T5 DNA polymerase substantially reduced in 3'-to-5' exonuclease activity.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following Claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

What is claimed is:

1. In a method for producing a soluble protein comprising the steps of:
   a) culturing a transformed *E. coli* cell containing a heterologous DNA molecule,
   b) expressing the protein, and
   c) isolating said protein from said host cell, the improvement which comprises using as the heterologous DNA molecule one comprising:
      (1) a structural gene encoding a soluble protein having a leader sequence containing at least the amino acid sequence:

NH$_2$-Met-Lys-Ile-Ala-Val-Val-Asp-Lys-Ala-Leu;
      and (2) a promoter heterologous to said structural gene, wherein said promoter and said structural gene are in such position and orientation with respect to each other that the structural gene for expression in said *E. coli* cell is under control of said promoter.

2. The method of claim 1, wherein the heterologous DNA molecule further comprises:
   (3) an origin of replication which maintains the structural gene/promoter/origin of the replication combination in said *E. coli* cell.

3. The method of claim 1, wherein the leader sequence is the amino acid sequence:

NH$_2$-Met-Lys-Ile-Ala-Val-Val-Asp-Lys-Ala-Leu-

Asn-Asn-Thr-Arg-Tyr-Asp-Lys-His-Phe-Gln-

Leu-Tyr-Gly-Glu-Glu-Val-Asp-Val-Phe-His.

4. The method of claim 2, wherein the leader sequence is the amino acid sequence:
   NH$_2$-Met-Lys-Ile-Ala-Val-Val-Asp-Lys-Ala-Leu- Asn-Asn-Thr-Arg-Tyr-Asp-Lys-His-Phe-Gln- Leu-Tyr-Gly-Glu-Glu-Val-Asp-Val-Phe-His.

5. The method of claim 1, wherein the promoter is inducible.

6. The method of claim 5, wherein the promoter is a lac promoter.

7. The method of claim 5, wherein the promoter is a tac promoter.

8. The method of claim 5, wherein the promoter is a lambda P$_L$ promoter.

9. In a method for producing a protein comprising the steps of:
   a) culturing a transformed *E. coli* cell containing a heterologous DNA molecule; and
   b) isolating said protein from said host cell, the improvement which comprises using as the heterologous DNA molecule one comprising:
      (1) a structural gene encoding a protein having a T5 DNA polymerase activity with a substantially reduced 3'-to-5' exonuclease activity, and a leader sequence containing at least the amino acid sequence:

NH$_2$-Met-Lys-Ile-Ala-Val-Val-Asp-Lys-Ala-Leu,
      and (2) a promoter heterologous to said structural gene, wherein said promoter and said structural gene are in such position and orientation with respect to each other that the structural gene for expression in said *E. coli* cell is under control of said promoter.

10. The method of claim 9, wherein the heterologous DNA molecule further comprises:
    (3) an origin of replication which maintains the structural gene/promoter/origin of the replication combination in said *E. coli* cell.

11. The method of claim 9, wherein the leader sequence is the amino acid sequence:

NH$_2$-Met-Lys-Ile-Ala-Val-Val-Asp-Lys-Ala-Leu-

Asn-Asn-Thr-Arg-Tyr-Asp-Lys-His-Phe-Gln-

Leu-Tyr-Gly-Glu-Glu-Val-Asp-Val-Phe-His.

12. The method of claim 10, wherein the leader sequence is the amino acid sequence:

NH$_2$-Met-Lys-Ile-Ala-Val-Val-Asp-Lys-Ala-Leu-

Asn-Asn-Thr-Arg-Tyr-Asp-Lys-His-Phe-Gln-

Leu-Tyr-Gly-Glu-Glu-Val-Asp-Val-Phe-His.

13. The method of claim 9, wherein the promoter is inducible.

14. The method of claim 13, wherein the promoter is a lac promoter.

15. The method of claim 13, wherein the promoter is a tac promoter.

16. The method of claim 13, wherein the promoter is a lambda P$_L$ promoter.

17. The method of claim 9, wherein the exonuclease activity is less than or equal to 1 unit/mg protein.

18. The method of claim 17, wherein the exonuclease activity is less than 0.1 unit/mg protein.

19. The method of claim 18, wherein the exonuclease activity is less than 0.003 unit/mg protein.

20. The method of claim 19, wherein the exonuclease activity is less than 0.0001 unit/mg protein.

21. In a method for producing a protein comprising the steps of:
   a) culturing a transformed *E. coli* cell containing a heterologous DNA molecule and
   b) isolating said protein from said host cell, the improvement which comprises using as the heterologous DNA molecule one comprising:
      (1) a structural gene encoding a protein having a T5 DNA polymerase activity, an exonuclease activity of less than or equal to 1 unit/mg protein, and a leader sequence which is the amino acid sequence:

NH₂-Met-Lys-Ile-Ala-Val-Val-Asp-Lys-Ala-Leu-

Asn-Asn-Thr-Arg-Tyr-Asp-Lys-His-Phe-Gln-

Leu-Tyr-Gly-Glu-Glu-Val-Asp-Val-Phe-His;

(2) an inducible promoter selected from the group consisting of a lac promoter, a tac promoter, and a lambda P$_L$ promoter which is heterologous to said structural gene, wherein said inducible promoter and said structural gene are in such position and orientation with respect to each other that the structural gene for expression in said *E. coli* cell is under control of said promoter; and
      (3) an origin of replication which maintains the structural gene/promoter/origin of the replication combination in said *E. coli* cell.

22. The method of claim 21, wherein the exonuclease activity is less than 0.1 unit/mg protein.

23. The method of claim 22, wherein the exonuclease activity is less than 0.003 unit/mg protein.

24. The method of claim 23, wherein the exonuclease activity is less than 0.0001 unit/mg protein.

25. In a method for producing a soluble protein comprising the steps of:
   a) culturing a transformed *E. coli* cell containing a heterologous DNA molecule;
   b) expressing the protein; and
   c) isolating said protein from said host cell,
   the improvement which comprises using as the heterologous DNA molecule one comprising:
      (1) a structural gene encoding a soluble T5 DNA polymerase having a leader sequence which is the amino acid sequence:

NH₂-Met-Lys-Ile-Ala-Val-Val-Asp-Lys-Ala-Leu-

Asn-Asn-Thr-Arg-Tyr-Asp-Lys-His-Phe-Gln-

Leu-Tyr-Gly-Glu-Glu-Val-Asp-Val-Phe-His;

(2) an inducible promoter selected from the group consisting of a lac promoter, a tac promoter, and a lambda P$_L$ promoter heterologous to said structural gene, wherein said inducible promoter and said structural gene are in such position and orientation with respect to each other that the structural gene for expression in said *E. coli* cell is under control of said promoter, and
      (3) an origin of replication which maintains the structural gene/promoter/origin of the replication combination in said *E. coli* cell.

26. In a method for producing a soluble protein comprising the steps of:
   a) culturing a transformed *E. coli* cell containing a heterologous DNA molecule;
   b) expressing the protein; and
   c) isolating said protein from said host cell,
   the improvement which comprises using as the heterologous DNA molecule one comprising:
      (1) a structural gene encoding a protein having a T5 DNA polymerase activity, an exonuclease activity of less than or equal to 1 unit/mg protein, and a leader sequence which is the amino acid sequence:

NH₂-Met-Lys-Ile-Ala-Val-Val-Asp-Lys-Ala-Leu-

Asn-Asn-Thr-Arg-Tyr-Asp-Lys-His-Phe-Gln-

Leu-Tyr-Gly-Glu-Glu-Val-Asp-Val-Phe-His;

(2) an inducible promoter selected from the group consisting of a lac promoter, a tac promoter, and a lambda P$_L$ promoter heterologous to said structural gene, wherein said inducible promoter and said structural gene are in such position and orientation with respect to each other that the structural gene for expression in said *E. coli* cell is under control of said promoter; and
      (3) an origin of replication which maintains the structural gene/promoter/origin of the replication combination in said *E. coli* cell.

27. The method of claim 26, wherein the exonuclease activity is less than 0.1 unit/mg protein.

28. The method of claim 27, wherein the exonuclease activity is less than 0.003 unit/mg protein.

29. The method of claim 28, wherein the exonuclease activity is less than 0.0001 unit/mg protein.

* * * * *